(12) United States Patent
Brück et al.

(10) Patent No.: US 11,447,801 B2
(45) Date of Patent: Sep. 20, 2022

(54) PROCESS FOR THE CELL-FREE ENZYMATIC PRODUCTION OF 10-HYDROXYSTEARIC ACID (10-HSA) FROM BIO-BASED OILS FOR LUBRICANT FORMULATION

(71) Applicant: TECHNISCHE UNIVERSITÄT MÜNCHEN, Munich (DE)

(72) Inventors: Thomas Brück, Moosinning (DE); Jan Lorenzen, Kiel (DE)

(73) Assignee: TECHNISCHE UNIVERSITÄT MÜNCHEN, Munich (DE)

( * ) Notice: Subject to any disclaimer, the term of this patent is extended or adjusted under 35 U.S.C. 154(b) by 37 days.

(21) Appl. No.: 16/651,185

(22) PCT Filed: Sep. 27, 2018

(86) PCT No.: PCT/EP2018/076319
§ 371 (c)(1),
(2) Date: Mar. 26, 2020

(87) PCT Pub. No.: WO2019/063718
PCT Pub. Date: Apr. 4, 2019

(65) Prior Publication Data
US 2020/0270646 A1    Aug. 27, 2020

(30) Foreign Application Priority Data
Sep. 29, 2017  (EP) ..................... 17194095

(51) Int. Cl.
*C12P 7/42* (2006.01)
*C10M 105/24* (2006.01)

(52) U.S. Cl.
CPC ............. *C12P 7/42* (2013.01); *C10M 105/24* (2013.01); *C10M 2207/128* (2013.01)

(58) Field of Classification Search
CPC ... C12P 7/42; C10M 105/24; C10M 2207/128
See application file for complete search history.

(56) References Cited

U.S. PATENT DOCUMENTS

| 6,008,169 A * | 12/1999 | Kaneko ................ C10M 129/36 508/501 |
| 2011/0028679 A1* | 2/2011 | Mao ........................ C08G 69/28 528/345 |
| 2012/0034190 A1* | 2/2012 | Apt ........................... A61P 13/12 424/93.3 |

FOREIGN PATENT DOCUMENTS

| KR | 101556362 A | 9/2015 |
| KR | 101749429 B1 | 6/2017 |

(Continued)

OTHER PUBLICATIONS

Kim, B.-N., Joo, Y.-C., Kim, Y.-S., Kim, K.-R., Oh, D.-K., "Production of 10-hydroxystearic acid from oleic acid and olive oil hydrolysate by an oleate hydratase from Lysinibacillus fusiformis", Appl. Microbiol. Biotechnol., 2012, 929-937 (Year: 2012).*

(Continued)

*Primary Examiner* — James C Goloboy
(74) *Attorney, Agent, or Firm* — Saliwanchik, Lloyd & Eisenschenk

(57) ABSTRACT

The present invention relates to an enzymatic process for the modification of free fatty acids (FFAs) derived from renewable feedstocks of bio-based oils. Specifically, the invention describes the hydrolysis of any bio-based oil, such as high oleic sunflower oil (HOSO), to FFAs, containing high amounts of oleic acid (OA), which is further hydrated to 10-hydroxystearic acid (10-HSA).

19 Claims, 15 Drawing Sheets

Figure 2:
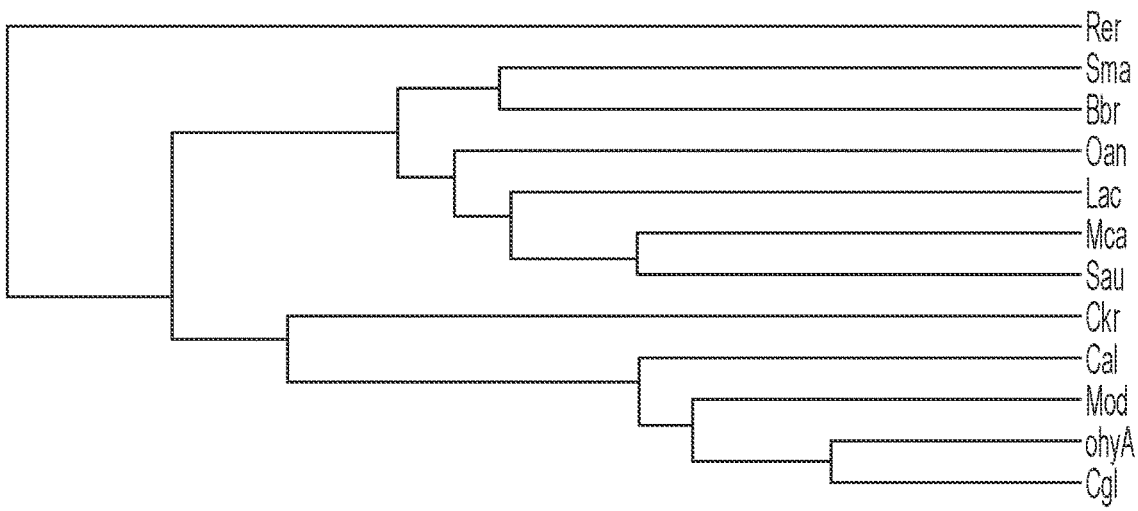

Specification includes a Sequence Listing.

(56) References Cited

FOREIGN PATENT DOCUMENTS

| WO | 2016151115 A1 | 9/2016 | |
|---|---|---|---|
| WO | WO-2016151115 A1 * | 9/2016 | ............ C12P 7/6436 |

OTHER PUBLICATIONS

Kang, W.-R., Seo, M.-J., Shin, K.-C., Park, J.-B. Oh, D.-K., "Comparison of Biochemical Properties of the Original and Newly Identified Oleate Hydratases from Stenotrophomonas maltopholia", Appl. Environ. Microbiol. 2017, 1-11 (Year: 2017).*

Hudson, J.A., MacKenzie, C.A.M., Joblin, K.N., "Conversion of oleic acid to 10-hydroxystearic acxid by two species of ruminal bacteria", Appl. Microbiol. Biotechnol., 1995, 44, 1-6 (Year: 1995).*

Demming, R.M. et al., "Optimized Reaction Conditions Enable the Hydration of Non-natural Substrates by the Oleate Hydratase from Elizabethkingia meningoseptica" ChemCatChem, Jan. 2017, pp. 758-766, vol. 9.

Engleder, M. et al., "On the current role of hydratases in biocatalysis" Applied Microbiology and Biotechnology, May 2018, pp. 5841-5858, vol. 102.

Hudson, J.A. et al., "Conversion of oleic acid to 10-hydroxystearic acid by two species of ruminal bacteria" Appl Microbiol Biotechnol, 1995, pp. 1-6, vol. 44.

Kang, W.R. et al., "Comparison of Biochemical Properties of the Original and Newly Identified Oleate Hydratases frorr Stenotrophomonas maltophilia" Applied and Environmental Microbiology, May 2017, pp. 1-11, vol. 83, Issue 9.

Kim, B.N. et al., "Production of 10-hydroxystearic acid from oleic acid and olive oil hydrolyzate by an oleate hydratase from Lysinibacillus fusiformis" Appl Microbiol Biotechnol, 2012, pp. 929-937, vol. 95.

Koppireddi, S. et al., "Combined Biocatalytic and Chemical Transformations of Oleic Acid to w-Hydroxynonanoic Acid and a,w-Nonanedioic Acid" Adv. Synth. Catal., 2016, pp. 3084-3092, vol. 358.

Kwon, H.T. et al., "Complete genome sequence of *Stenotrophomonas* sp. KCTC 12332, a biotechnological potential bacterium" Journal of Biotechnology, Jul. 2017, pp. 27-30, vol. 256.

Lorenzen, J. et al., "Rhodococcus erythropolis Oleate Hydratase: a New Member in the Oleate Hydratase Family Tree-Biochemical and Structural Studies" ChemCatChem, 2018, pp. 407-414, vol. 10.

O'Connell, K.J. et al., "Identification and characterization of an oleate hydratase-encoding gene from Bifidobacterium breve" Bioengineered, 2013, pp. 313-321, vol. 4.

Schmid, J. et al., "Biocatalytic study of novel oleate hydratases" Journal of Molecular Catalysis B: Enzymatic, 2016, pp. S243-S249, vol. 133.

Serra, S. et al., "Use of Lactobacillus rhamnosus (ATCC 53103) as Whole-Cell Biocatalyst for the Regio- and Stereoselective Hydration of Aleic, Linoleic, and Linolenic Acid" Catalysts, Mar. 2018, pp. 1-14, vol. 8.

Todea, A. et al., "Increase of stability of oleate hydratase by appropriate immobilization technique and conditions" Journal of Molecular Catalysis B: Enzymatic, 2015, pp. 40-47, vol. 119.

UniProt/Swiss-Prot, XP-02775789, Oct. 2017, pp. 1-2.

* cited by examiner

```
Rer  RELGNDAGFINRGGRMLNEETYENLMDVLSAVPSLDNPG-KSVTDDILDEDHAHPTHDVA      120
Sma  -LKVPEKGFVIRGGREM-EDHFECLWDLFRSIPSLEIED-ASVLDEFWLNKDDPNVSLQ      124
ohyA -AGNPTDGYIIRGGREM-DMTYENLWDMFQDIPALEMPAYSVLDEIRLINDNSNYSKA      165
Mca  -ILNPERGYIMRGGREM-ENHFECLWDLFRSVPSLEVED-ASVLDEFWLNKEDPNYSKC      124
Bbr  -LDIPGLGYVMRGGREM-DNHFEVMWDLFRSIPSIETEG-VSVLDEYWLNKEDPNYSLC      124
Ckr  -AGMNQEGFIARGGREM-GQHFECEWDIMKDVPAIEMPAPHTVLDEFNKVNEEDPNISNC      141
Oan  -ILDEHKGFVIRGGREM-EAHFETLWDLFRSIPSLDTPD-ASVLDEMWLHKKDPSRNPC      124
Mod  -AGNAQEGYTVRGGREM-DMTYENLWDIFQDIPALELPKPYSVLDEYRLINDNDPNYSKS      165
Sau  -ENMPLKGYVVRGGREM-ENHFECLWDLFRSIPSLEIDR-ASVLDEFWLNKEDPNYSRC      124
Cgl  -AGNAKDGYIIRGGREM-DMTYENLWDMFQDIPALELPAPYSVLDEIKRLMDNDPNYSKA      165
Cal  -SGNARDGYLIRGGREL-EMVENLWDIFQDIPALEMPAPYSVLDEFRLLNDNDPNYSKA      165
Lac  -ADRPNAGFVVRGGREM-ENHFECLWDMYRSIPSLEVPG-ASYLDEYVWLDKEDPNSSNC     124
        * ;:   ****  ;     * *;: ;.*  :*   ;* ;::;:*  :*

Rer  RLIDRDGIRNKGENDYKHMQDTNKDRYLLLKIMTMPESDEAKLDDISIEQWFEETPHFT      180
Sma  RAIINRGEDAHTDGL---FTLIEQAQKDIIALFL---ATRQEMENKRINEVLGR--DFLD      176
ohyA RLINNKGEIK-DFSK---FGLNKMDQLAIIRLLL---RNKEELDDLTIEDYFSE--SFLK      216
Mca  RVIENRGQRLESDGK---MTLIKKANKELIQLCL---MKEEQLNDVKISDVFSK--DELD      176
Bbr  RATKOLGKDAGLGGK---FGLSDKASMEIMKLFF---TPDEDLYDKPITDFFDD--EVLN      176
Ckr  RIISNQAQTRLKNPK---LELSKKAQLQIVKLLL---AKEEDTYYKTIEDWFGK--DFLE      193
        :  *  :  .          :    : : :      ;.         *
```

From Figure 1-1

```
Rer  IVTGLDYENVRTGEKCRIDVAEGDEVFDTNGSITDSSIGDLDTPIVED-----MRYAPS     323
Sma  QATRI--HWMHDGVASGVDLGADDLLFMTIGSITENSDNGDHHTAARLN-----EGPAPA     315
ohyA VVEGI--ITEQDGKEVKIPVGKNDYVIVTTGSMTEDTFYGNNKTAPIIGIDNSTSGQSAG    360
Mca  VAKAI--DIVRRGNEESIPLITENDLVFVTNGSITESTTYGNDTPAPPT-----SKPGGA    315
Bbr  LAVRI--DVSQEGEKKSSIDLITENDLVFTINGGCVENSTMGSQNSPAAWNP--DLKPGG    351
Ckr  TVTGI--VTNKE----TIPTRSQDIVIVTNGSLJESTGYGDMFVPEFK-----KTPGPA    328
Oan  LARRL--VMTVGGEPKTIELTENDVFVTNGSITESSTFGNDHPAPIE-----TGHGGA    315
Mod  LVKGL--LVNQGGQFPRIEMNEQDFVITTGSMTEDTSYGTNTTVPIPKVDNTTSGKSPG   360
Sau  IAREI--LIHRHGKAESIKLTVDDLVFNGSTIESTYGNDTPAPPT-----DELGGS      315
Cgl  TVEGI--ITEQNGEEVKIPISKEDVIVTTGSMTESTFYGDNNTVPEVTIDNSSAGQSAG   360
Cal  VVKGI--ITQQEDKEVTIAVTENEVIVTTGSMFEDTHYGDNINAPIVAIDIKSGESDG   360
Lac  IAKKI--VMTQNGKDKEIDLTHENDIVFVTNGSITESSTYGDQNTPAPIT-----NAKGDS   314
                *      *: *      * *;:    ::*

Rer  ALLWKQATEHFYDLGPDKFFGDRAQSEMT-SFTVTTSSHELINEIS---RITKQLP----     376
Sma  WDLMRRLAAKDDAFGPRDVFGAHIPETKME-SATVTTLDARIPAYIQ---KIAKRDPFSG    371
ohyA WKLMWNLAAKSEIFGKPEKFCSNIEKSAME-SALLTC--KPSALIDKLKEYSVNDPYSG    416
Mca  MQLWENLSTQCEEFGPAKFYKDLPEKSWFVSATAITNNKEVIDYIQ---KICKRDPLSG    372
Bbr  WDMWRRIAEQDPSFGHPEKFCSDPNATKWM-SATVTTLDDEIPPYIQ---KICKRDPFSG    407
Ckr  WSLMWNTAERKAPNCGPERFCSDPFSTVWE-SISENFYDGYDNPFTQKLKELTHRDVFNG    387
```

Figure 3:
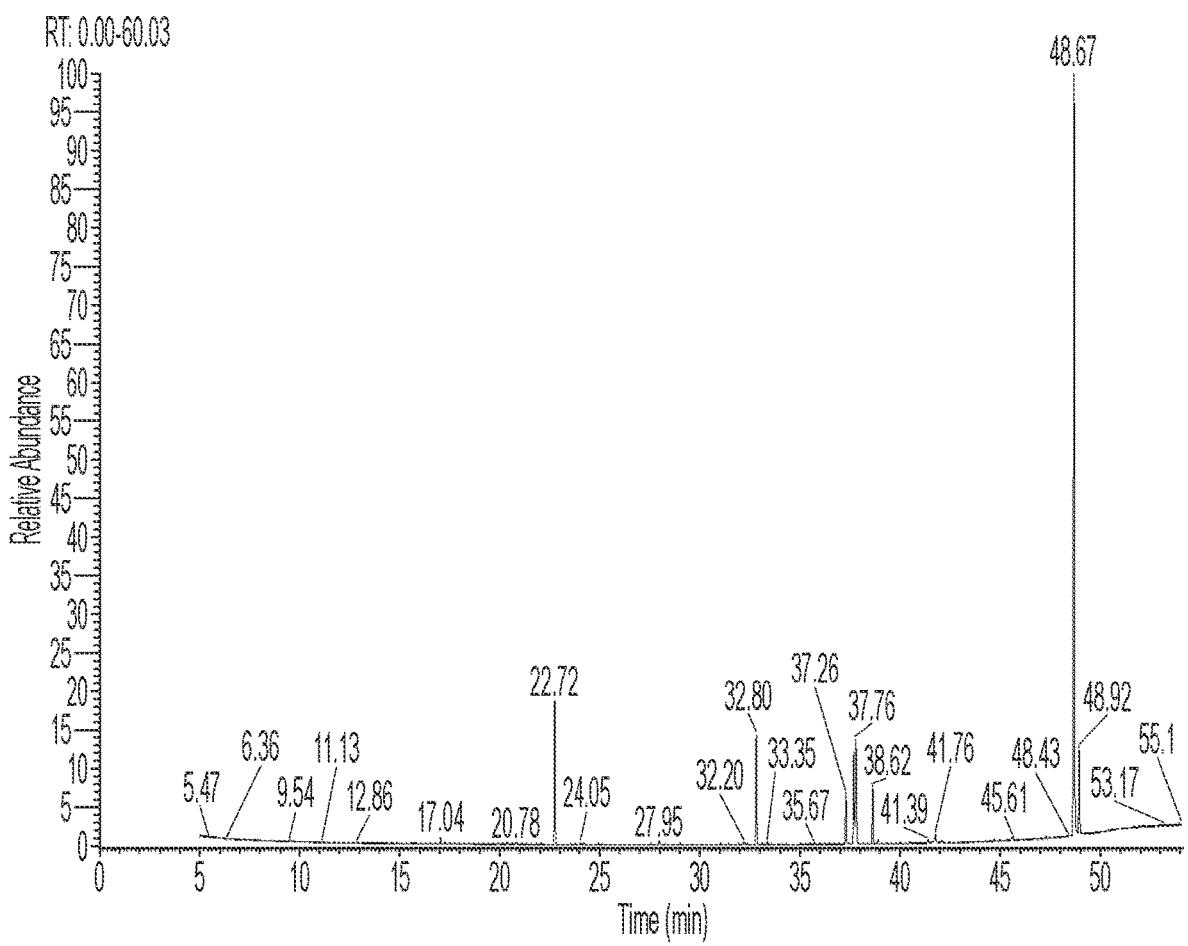

To Figure 1-3

Figure 1-3:

```
Oan  RATEGRGDPIPEMAD---LPLTPKAVEEMLKLAL---TPESALDDKRIDECFGE--EFFA   176
Mod  RETHQLGEIK-DFSQ---FGLSKKDQMALIKLLL---RRKEELBDITIEQYFHS--SFLE   216
Sau  RVIEKQGQRLVDBGD---FTLRTAIKEILDLCL---TNEEDLBDVKITBVFSD--DFFN   176
Cgl  RLIHNQGIK-DESK----FGLEKKBQLAIVKLLL---RKKKEELBDLIEDYFSE--SFLN   216
Cal  RLIHNNGEIQ-DFSK---FGLDKLBQLAIVKLLL---RKKEELBDVVESYFSD--SFFK   216
Lac  RLIYNRGDRLPSDGQ---YGLGKCA-NEIVKLIM---TPEKEIEGQTIEEFFSD--EFFK   175
                *                     *                    :
Rer  ---GNALNTFVDSNVLLSIVHQPHVHAQKEN-EGVTWGYCLFPRKGDYVKKPIEMT   432
Sma  KVTNGGIVSVRDSRWLMSWTVNRQPHFKNQPKD-QIVWWVYSLFVDTPGDYVKKPMQDCT   430
ohyA KTVTGGIITHTDSNWLMSFTCNRQPHFPEQPDD-VLVLWVYALFMDKGNYIKKTMLECT   475
Mca  RTVTGGIVTVDSNWQLSFTLNRQQFRNQPDD--QVSWIIYALYSDERGERTNKTVECS   431
Bbr  KVTAGGIVTVQQSNWILMSWTLNRPQQFRDQPKD--QLCVWVYGLFPDRKPGNYVKKPMECT   466
Ckr  RAVTAGIITAQDSPWLCSIVHRPQPQFPGQDG-LCVAMAYGLHWWKKGTVTGKPMLECT   446
Oan  RIVTGGPCNFKDSNWLYGYIMSRQPHFKAQDESQKLVWLVYGLFSDKPGNYVKKKIRECA   432
Mod  KTVTGGIITHTDSNWLMSFTCNRQPHFPTQPDD--ILVLWVYALFMDKGNYIKKTMEACT   475
Sau  KTVTGGIITNDSAWQISFTINRQQFKDQPKN--EISWIIYALYSDVNGDYIKKPITECS   431
Cgl  RTATGGIITNDSNWVMSFTCNRQPHFPEQPDD--ILVLWVYALFMDKGNYIKKTMEQCT   475
Cal  KSATGGIVTITHDSNWLMSFTINRQPHFPEQPDD--ILVLWVYALFMDKNIGNYSKKTMPQCT   475
Lac  KVNTGGIITIVDSNWELSFTIHRQPHFKSQNPD--QIVWWIYALYSDEGNYIKKRIVDCT   430
        *   ** ::: * : :                 * :                **

Oan  WTLMKNLAAQHPAFGREPEKFECEDIPDANWTISANVTLLDDKIVPWIE---KMTGRDPRDG   372
Mod  WSLMKNLAAKSPVFGRFEKFCSNIERKSSWE-SATLTC--RPSPLIDKLIKEYAVNDPYSG   416
Sau  WTLMKRNILARQSPEFGNFDKFCQNIPQKSWFVSANSTTNKDIIDTIE---SICKRDPLAG   372
Cgl  WKLMKRNLAAKSEVFGKPEKFCSHIERKSSWE-SAILTC--RPSAFTEKLKELCVNDPYSG   416
Cal  WQLMKNLATKSIEFGKPEKFYSSVVKSSWE-SAILTC--RPSAFTEKIKEYCVNDPYSG   416
Lac  WKLMENLAKQDPAFGHPDVFCENLPERSWFVSATATLENKKLAPYFE---RLTKRSLYDG   371
         * .* *    .:   .          **:     *  * * .

Rer  KAAVTMER-------                                                559
Sma  AATGRLRDGKELGIPGPV-PLRN------LLMNKLDKTQIGGLREFKLVQED------    589
ohyA KAAKTLNDDKPFVGEG-------------LLRKVLKGTYEHVLPAGAAEEEHESFIAEHV   634
Mca  HALSVLANDGKKLDEIDMP--FYERVEKRLLKASGTFEELLEEANLI------------   589
Bbr  NATVIK.RDGAPVTDMKLN--FIEKAVVKKVLKKLDGTDIATLLREYHVI--------    625
Ckr  HSASAMNDG--KLPGEK----------------LLRKELKNTVYENIIPKGSSH-----    591
Oan  SALYYLNDRKKLDEIQLP--FVARLLGKVAMKIEGTYLEELLKDAKLV---------    591
Mod  KAAHALNDBQPIVGEA--------------LLRKELQGTYEHILPTVEKRKDQESFFVEQY   634
Sau  DAIYELMNDHQDLREITKDSKIQKLALAGFLKKLGTYIESLLKEHKL--------    591
Cgl  KATQALNDYKPELGEG--------------ILRKILKGTYEHIIVNRPEEKEHESFL---   630
Cal  KAAKALNDYKPFPGES--------------VLKRVLKNTYEHIIPEGVEDEEQHDSFLTEQL    634
Lac  RAMYYMSDKKKLABQDMP-LPEKLAVTKTGMRKIKKTWVEERLLKEANLV--------    591
        :: :                :

Rer  GREMLEETLGHLEALDESGTLAARRQEIMDSVVNSIPSHMPYASALFNRRAVGDRPLVVP   492
Sma  GEEITREWLYHLGVPVEEIDELAA----T-GAKTVPVMPYITAFFMPRQAGDRPDVVP   484
```

Figure 1-4:

From Figure 1-3

```
ohyA GDEILAELCYHLGIEDQL-ENVQK--------NTIVRTARMPYITSMMPRAKGDRPRVVP 527
Mca  GKEICEEMLYHNGVPEEKISALAA--------ECNTIPSMPYITAYTMPRKEGDRPLWP  484
Bbr  GEEICEEMLYHNGVPTDKIESLAK--------H-HANTVPVMPYITAFTMPRAAGDRPDVVP 520
Ckr  GEEILREFCYHEGVVDVE--KTIK--------HTKVRLAVMPYITSEFVPRGAGDRPBPVP  497
Oan  GAELCEEMLFNMGVPVEDIPALAR--------R-SASTVPCNMPYITSYTMPRAMGDRPLWP  486
Mod  GNEILAELCYHLGIIDSL-NQVVE--------NTIVRTAMPYITSMMPYITSMMPRAQGDRPQVVP 527
Sau  GNEICQEWLYHLGVPTDKIEDLAK--------H-ASNTIPVMPYITSYTMTRAIGDRPLWP  485
Cgl  GNEILAELCYHLGITDQL-DNVTE--------NTIVRTARMPYITSNMFNPRAMGDRPRRVP  527
Cal  GNEVLAELCFHIGLEDQI-AIIIK--------NTIVKTSEMPYITSMMPRAAGDREWVP    527
Lac  GKEILAEELLYHLGVPESQISELAS-------EENMNTVPVMPYITSYFMPRDGDRRDWP   485
     * *:.   *. ::  *    ::        *  *   *  *** ****   **
Rer  KHSKNLAFISQPAEL-PFDMFTEQYSVRCAQVAVYKELGIPEDKLDRKMHHYEKDPKVLA   551
Sma  DGAVNEAFIGQPAESKQRDCIFTEYSVRPMEAVTILDIERGVPE-VFNSTYDVRSLL     543
ohyA EGCNLGLVGQFVET-NNDVFTMESSVRTARIAVYKLLNLNKQVPD-INPLQYDIRHLL    585
Mca  HGSKNLAFIGNFAET-ERDIVFTTEYSVRTAMEAVIKLLEVDRGVPE-VEASVYDVRILL  542
Bbr  DGAVNFAFLGQFAET-PRDIFTTEYSMRTGMEAVTILLGVDRGVPE-VWGSVIDVRNLL   578
Ckr  AGSSTNLGFTGQFVET-PDDCVFTTEGSARIGQMAVYGLLNLNKRDIP--IYPVQYDIRALL 555
Oan  DGSKNLAFIGNFAET-EKDIVFTTEYSVRTAMEAVTILRNVDRGVPE-VFRASSFDVRVLM  544
Mod  EGCNLGLIGQFVET-HNDVFTMESSVRTGROAVYQLLNINKQVPD-IFPLQYDIRHLL    585
Sau  HQSQNLAFIGNFAET-ERDIVFTTEYSVRTAMESSVRTGMEAVYQLLNIDRGIPE-VINSTEDLRVLM 543
Cgl  EGCTNLGLVGQFVET-NNDVFTMESSVRTARIAVYNLLNLNKQVPD-INPLQYDIRHLL   585
Cal  NGSKNLGLVGQFVET-HNDVFTVDASIRTARIAVYKLLNLNKQVPD-IAAGQYDIRQLL   585
Lac  EGSINLAFIGNFAESPTRDIVFTTEYSVRPAMEAVTILNVDRGVPE-VFDSIYDIRQLL   544
     . :.   .:.:      .  :.   : *  :: .  *   .    *. * ohyA NKFREWVKGIRG  646
Mca  ------------
Bbr  ------------
Ckr  ------------
Oan  ------------
Mod  EKAKDWFKKLIG  646
Sau  ------------
Cgl  TRFQEWVKGVKD  642
Cal  EKLKGWAKELTH 646
Lac  ------------
```

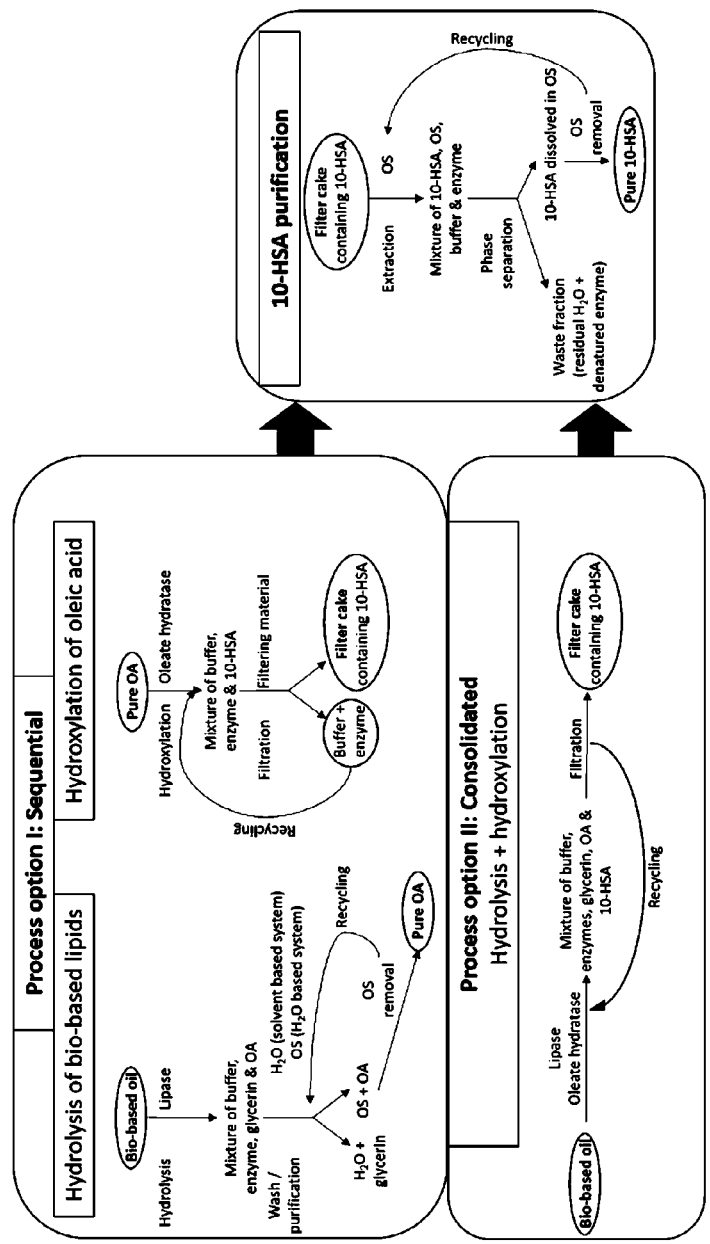
Figure 19: Scheme 2

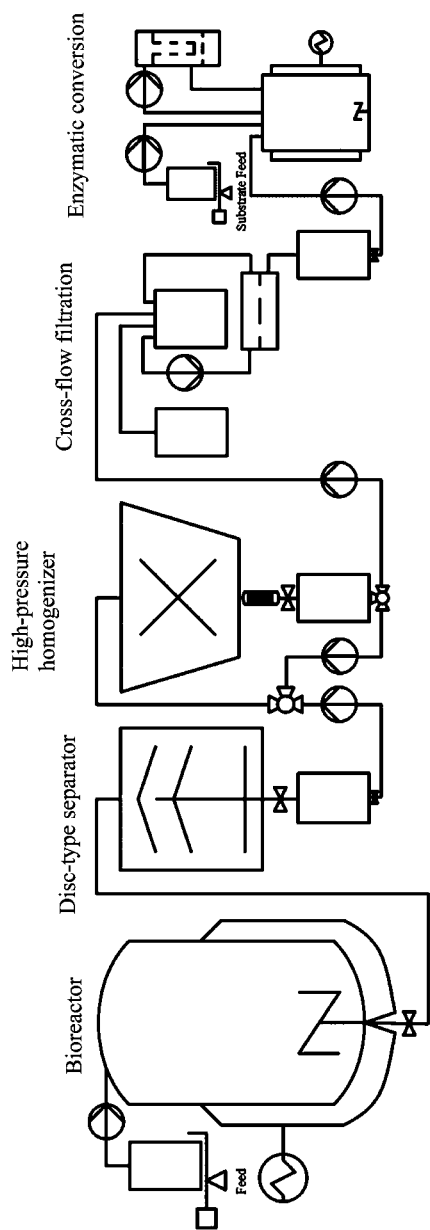
Figure 20: Scheme 5

PROCESS FOR THE CELL-FREE ENZYMATIC PRODUCTION OF 10-HYDROXYSTEARIC ACID (10-HSA) FROM BIO-BASED OILS FOR LUBRICANT FORMULATION

CROSS REFERENCE TO RELATED APPLICATIONS

This application is a National Stage Application of International Application Number PCT/EP2018/076319, filed Sep. 27, 2018; which claims priority to European Application No. 17194095.9, filed Sep. 27, 2017.

The Sequence Listing for this application is labeled "SeqList-19Mar20-ST25.txt", which was created on Mar. 19, 2020 and is 64 KB. The entire content is incorporated herein by reference in its entirety.

FIELD OF THE INVENTION

The present invention describes a method for the biological modification of natural, e.g., bio-based oils for lubricant/grease formulation. More particular, the invention describes an enzymatic process for the modification of free fatty acids (FFAs) derived from renewable feedstocks of bio-based oils. Specifically, the invention describes the hydrolysis of any bio-based oil, such as high oleic sunflower oil (HOSO), to FFAs, containing high amounts of oleic acid (OA), which is further hydrated to 10-hydroxystearic acid (10-HSA).

BACKGROUND OF THE INVENTION

Currently most additives used in lubricant or grease formulation are based on mineral oil feedstocks. Only a very low number of compounds used in lubricant production are from renewable feedstocks, for example 12-hydroxystearic acid isolated from castor oil.

The ability of different organisms to convert oleic acid to 10-hydroxystearic acid (10-HSA) was first described by Wallen et al.[1] in 1962 for the *Pseudomonas* strain 3266. The enzyme, responsible for this hydration reaction, was first isolated and characterized by Bevers et al.[2] in 2009 and defined as an oleate hydratase (EC 4.2.1.53). The oleate hydratase adds a hydroxyl group to the first position of the double bond in the chain of a mono unsaturated fatty acid in the absence of any co-factor that is consumed during the reaction (Scheme 3). A detailed description of the enzymatic reaction was published by Engleder et al.[3] in 2015. So far only two oleate hydratases have been crystalized[3-4] and most enzymatic reactions published only describe the production of 10-HSA from isolated oleic acid. At present, there are only two processes describing the conversion of complex oils to hydroxyl fatty acids[5] However, these publications are lacking two essential steps, the separation of the 10-HSA from the reaction mixture and the recycling of the applied catalyst. Therefore, the objective of the present invention is to provide a process overcoming these shortcomings. The sustainable process described herein demonstrates the enzymatic conversion of vegetable oil (e.g., HOSO), as a renewable feedstock for bio-based oils, to 10-HSA with a product separation and an integrated enzyme recycling for the first time.

The invention is directed to the bioconversion of bio-based oil to 10-HSA in a cell-free, enzymatic process. The first step of the cascade is the hydrolysis of the bio-based oil with a lipase to gain free fatty acids, especially oleic acid. The second step of the cascade is the hydration of the free oleic acid with an oleate hydratase.

SHORT DESCRIPTION OF THE FIGURES

FIG. 1: Sequence alignment of 14 different OHs from *Rhodococcus erythropulus* (Rre), *Staphylococcus aureus* (Sau), *Lysinibacillus fusiformis* (Lfu), *Macrococcus caseolyticus* (Mca), *Lactobacillus acidophilus* (Lac), *Ochrobactrum anthropi* (Oan), *Bifidobacterium breve* (Bbr), *Streptococcus pyogenes* (Spy), *Elizabethkingia meningoseptica* (Eme), *Myroides odoratus* (Mod), *Cellulophaga algicola* (Cal), *Stenotrophomonas maltophilia* (Sma), *Corynebacterium kroppenstedtii* (Ckr) and *Chryseobacterium gleum* (Cgl).

FIG. 2: Phylogenetic tree of the 14 aligned oleate hydratases in FIG. 1. Created by BLAST with the following settings: Tree method: Fast Minimum Evolution; Max Seq Difference: 0.85; Distance: Grishin (protein).

FIG. 3: GC-MS chromatogram after hydration of oleic acid (purity Z 80%; 35.4 mM) with the oleate hydratase from *Stenotrophomonas maltophilia* (final conc. 5 µM enzyme) for 90 min. RT 22.72: C12:0; RT 32.80: palmitic acid; RT 37.26: stearic acid; RT 37.76: oleic acid; RT 38.62: linoleic acid; RT 48.67: 10-hydroxystearic acid (10-HSA).

Figure 4:
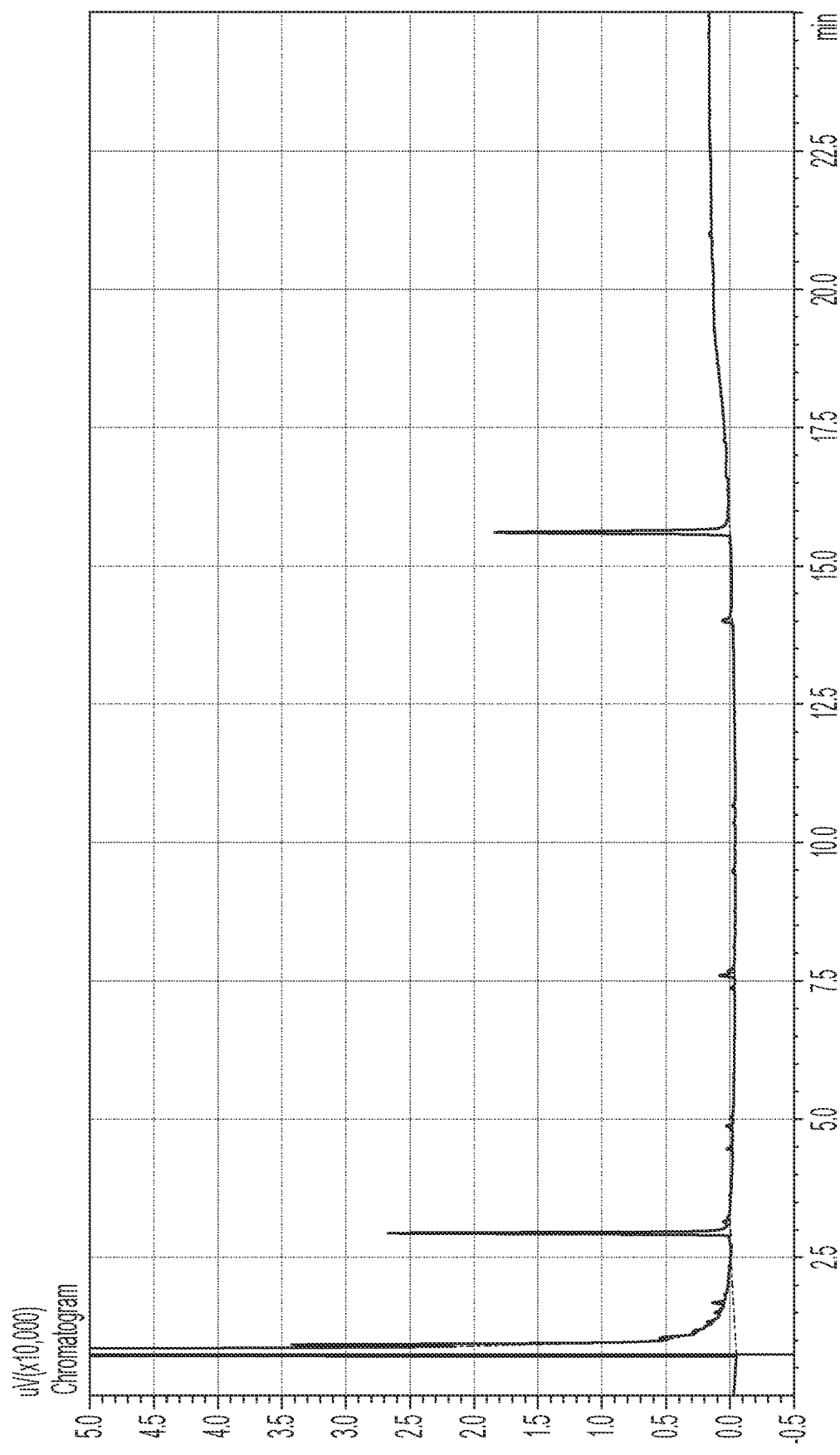

FIG. 4: GC-FID chromatogram after hydration of oleic acid (pure; 720 µM) with the oleate hydratase from *Rhodococcus erythropulus* (final conc. 5 µM enzyme) for 15 min. RT 7.5: oleic acid; RT 15.6: 10-hydroxystearic acid (10-HSA).

Figure 5:
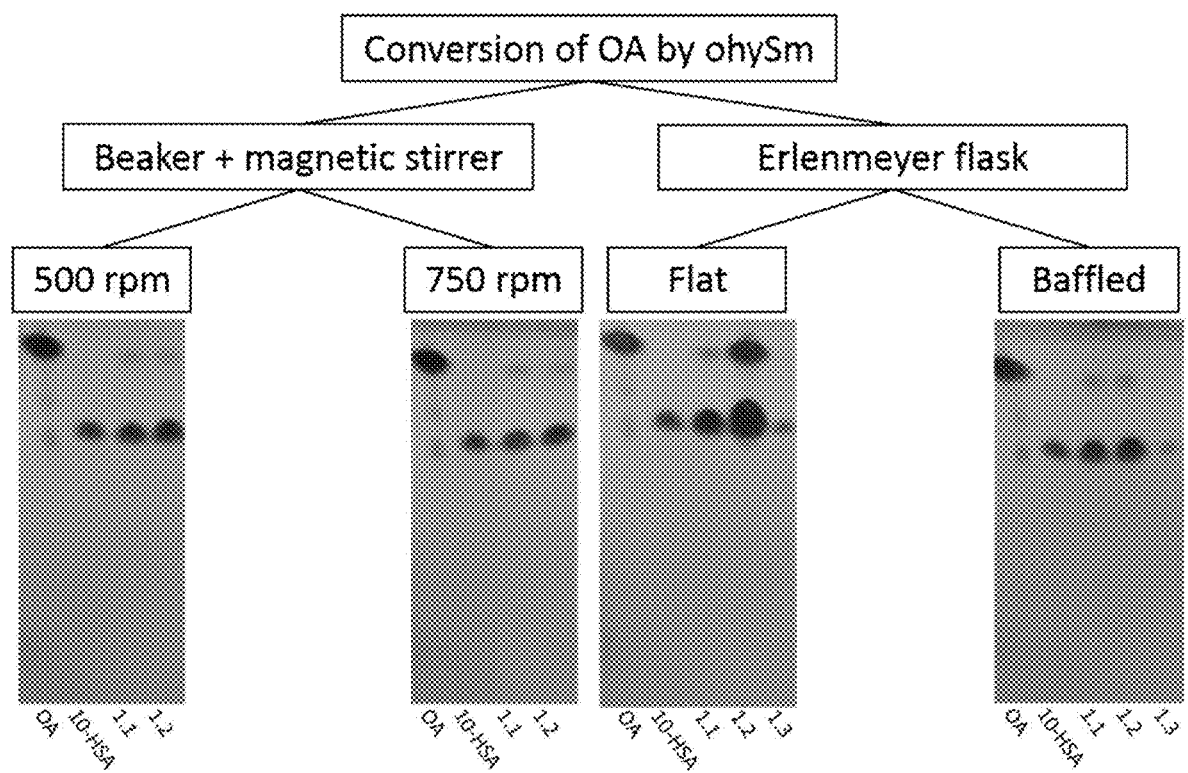

FIG. 5: Results of activity check of different samples after extraction on TCL plates after scale-up pre-testing of the conversion of oleic acid (OA) to 10-hydroxystearic acid (10-HSA) by the oleate hydrates (OH) from *Stenotrophomonas maltophilia* (ohySm) under different reaction conditions (Oleic acid (OA); 10-hydroxystearic acid (10-HSA); 1.1: $1^{st}$ conversion; 1.2: $2^{nd}$ conversion (recycled enzyme); 1.3: filtrate after $2^{nd}$ conversion).

Figure 6:
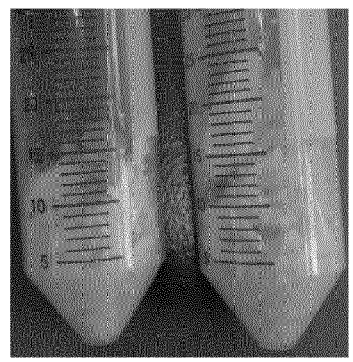

FIG. 6: Resulting pellets of the preparation 1 and 2 of the filtration test.

Figure 7:
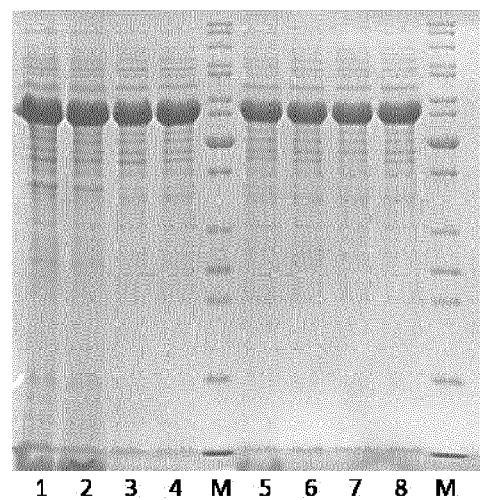

FIG. 7: SDS-PAGE analysis results of filtration test.

Figure 8:
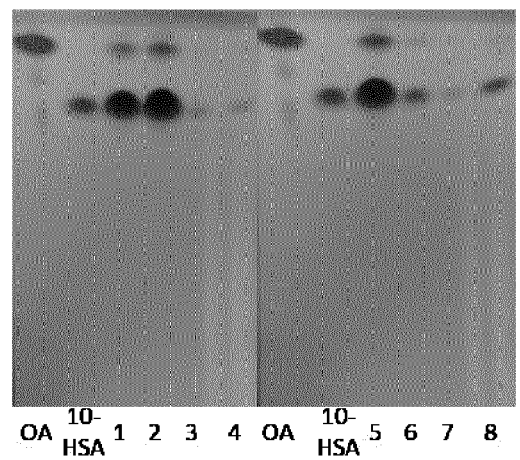

FIG. 8: Results of activity check of the samples by extraction and TCL of filtration test.

Figure 9:
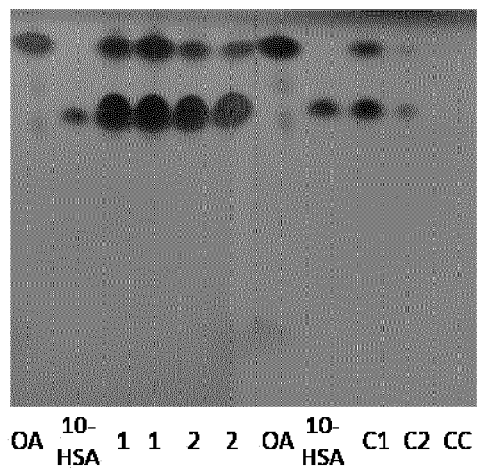

FIG. 9: Extraction results of the filter cake and the filtering cloth after direct extraction with EtOAc and spotting on TLC plates.

Figure 10:
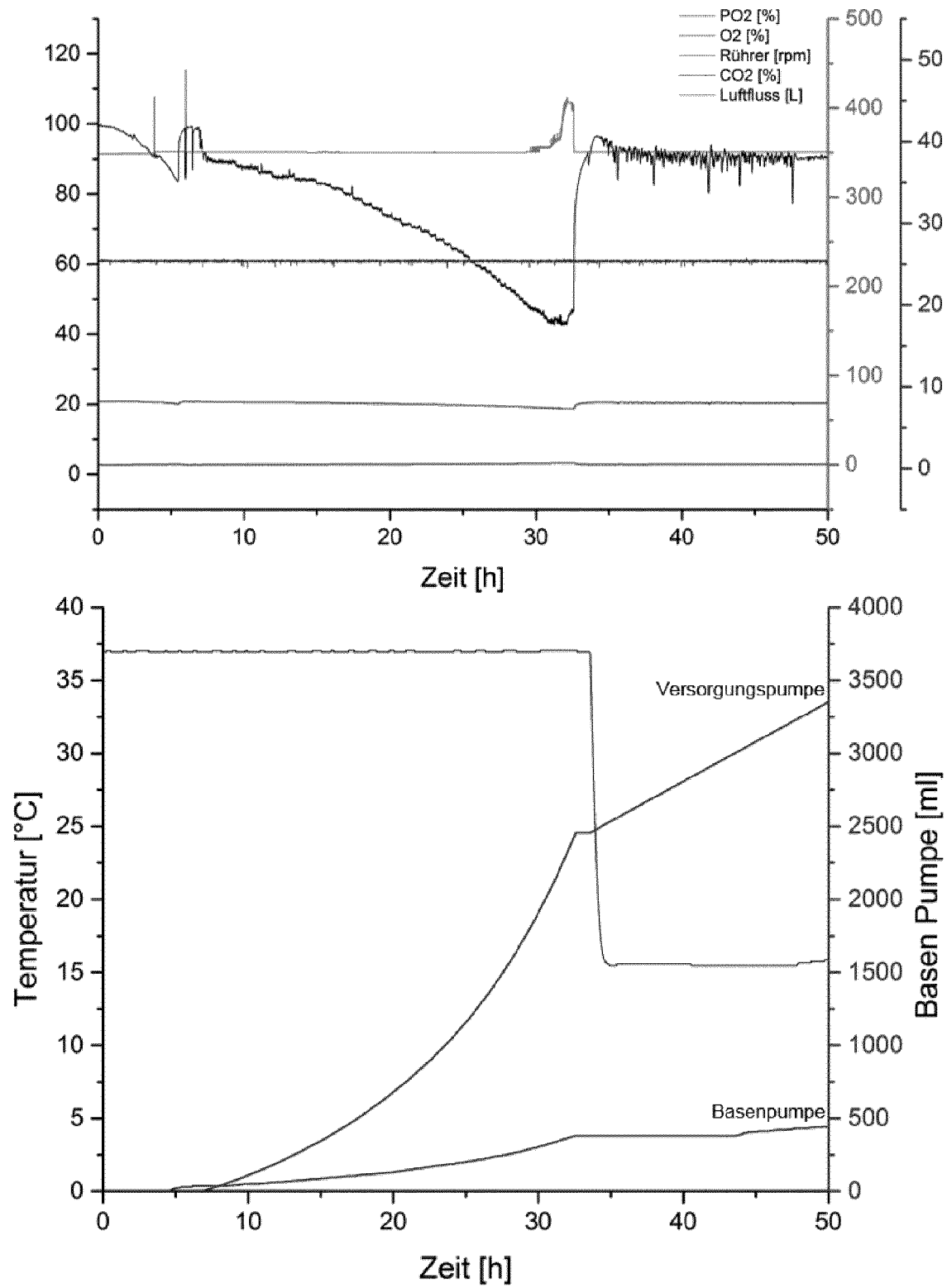

FIG. 10: Documentation of the fermentation process, monitoring all relevant fermentation parameters.

Figure 11:
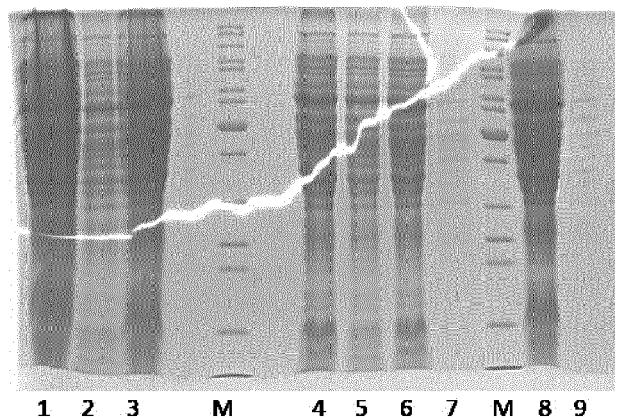

FIG. 11: SDS-PAGE corresponding to collected samples in Table. 6. Sample vol. 5 µl. M: page ruler unstained protein ladder (5 µl).

Figure 12:
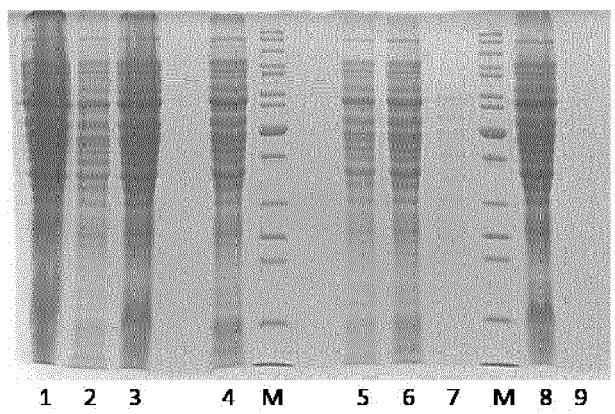

FIG. 12: SDS-PAGE corresponding to collected samples in Table. 6. Sample vol. 2.5 µl. M: page ruler unstained protein ladder (5 µl).

Figure 13:
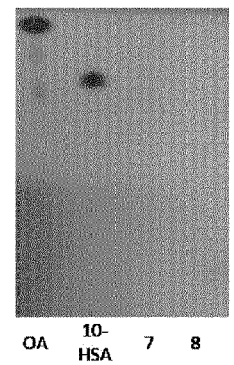

FIG. 13: TLC plate results after extraction test of samples 7 & 8 with OA and 10-HSA as standards.

Figure 14:
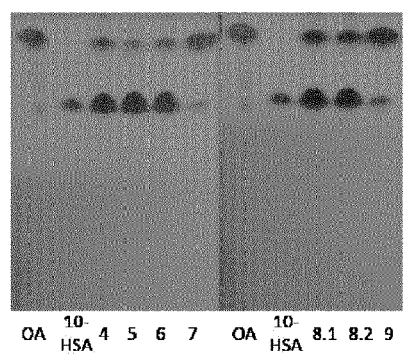

FIG. 14: 1 ml activity tests on TLC plate from collected samples with OA and 10-HSA as standards.

Figure 15:
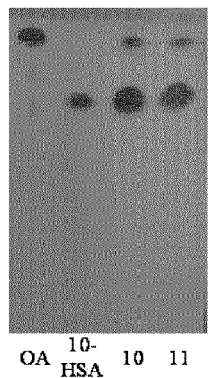

FIG. 15: Activity monitoring after 60 min reaction time from the two 4 L reactions with OA and 10-HSA as standards (TCL plate).

Figure 16:
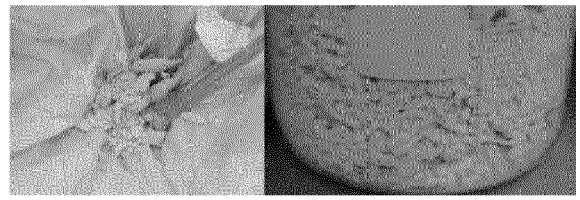

FIG. 16: Resulting filter cakes by filtration step with miracloth fabric (4 layers).

Figure 17:
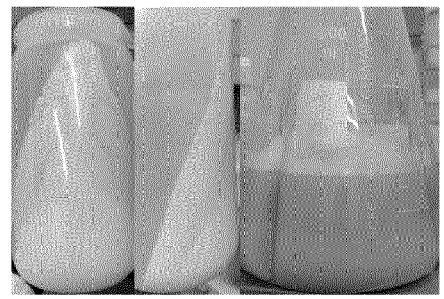

FIG. 17: Resulting pellet after separation of the product from the recycled enzyme solution.

Figure 18:
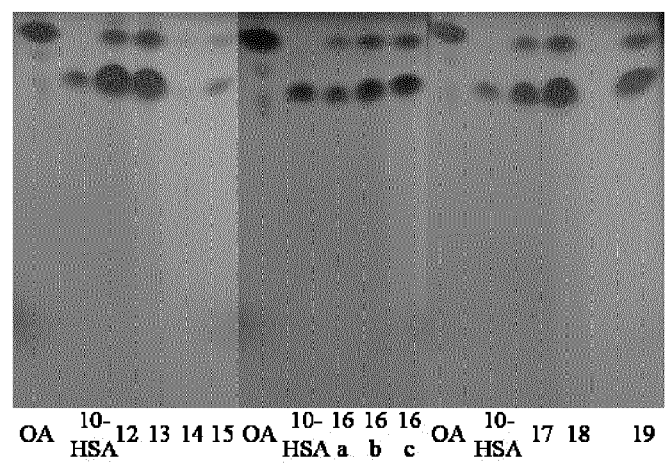

FIG. 18: TLC analysis from the separation approach.
FIGS. 19 and 20: Scheme 2 and 5.

DETAILED DESCRIPTION OF THE INVENTION

Before describing the invention in detail, it is deemed expedient to provide definitions for certain technical terms used throughout the description. Although the present invention will be described with respect to particular embodiments, this description is not to be construed in a limiting sense. Before describing in detail exemplary embodiments of the present invention, definitions important for understanding the present invention are given.

Definitions

As used in this specification and in the appended claims, the singular forms of "a" and "an" also include the respective plurals unless the context clearly dictates otherwise.

In the context of the present invention, the terms "about" and "approximately" denote an interval of accuracy that a person skilled in the art will understand to still ensure the technical effect of the feature in question. The term typically indicates a deviation from the indicated numerical value of ±20%, preferably ±15%, more preferably ±10%, and even more preferably ±5%.

It is to be understood that the term "comprising" is not limiting. For the purposes of the present invention the term "consisting of" is considered to be a preferred embodiment of the term "comprising of". If hereinafter a group is defined to comprise at least a certain number of embodiments, this is meant to also encompass a group which preferably consists of these embodiments only.

Furthermore, the terms "first", "second", "third" or "(a)", "(b)", "(c)", "(d)" etc. and the like in the description and in the claims, are used for distinguishing between similar elements and not necessarily for describing a sequential or chronological order. It is to be understood that the terms so used are interchangeable under appropriate circumstances and that the embodiments of the invention described herein are capable of operation in other sequences than described or illustrated herein.

In case the terms "first", "second", "third" or "(a)", "(b)", "(c)", "(d)" etc. relate to steps of a method or use there is no time or time interval coherence between the steps, i.e. the steps may be carried out simultaneously or there may be time intervals of seconds, minutes, hours, days, weeks, months or even years between such steps, unless otherwise indicated in the application as set forth herein above or below.

Herein below, various embodiments of the invention are explained in more detail. Wherever, respective alternatives in terms of ingredients in compositions, concentrations or amounts of ingredients, periods of time, the person skilled in the art would immediately understand that individual combinations can be made as long as these are technically possible or if not otherwise explicitly indicated.

The present invention describes a cell free, enzymatic reaction sequence to convert bio-based mono-, di- or triglycerides (oils) via a free fatty acid (FFA) intermediate (oleic acid) into 10-hydroxystearic acid (10-HSA).

Generally all animal, plant or microbial (i.e. triglycerides derived from bacteria, yeast, algae or fungi) oils are suitable as feedstocks for the described enzymatic conversion steps.

Bio-based triglycerides with an oleic acids content above 25% can be used for this process.

Examples are castor oil, tall oil or the triglyceride fraction from the oleaginous yeast *Rhodosporidium toruloides*.

In some embodiments bio-based triglycerides with an oleic acid content above 54% are used as feedstocks for the described process. A specific example is the triglyceride fraction of the oleaginous yeast *Cutaneotrichosporon oleaginosus* or rapeseed oil.

In further embodiments, oil feedstocks are bio-based oils with an oleic acid content above 75%. Examples are native sunflower oil or high oleic acid sunflower oil variants thereof (see Example 1 and Example 2).

Subject-matter of the present application is a process for the cell-free enzymatic production of 10-hydroxystearic acid (10-HSA) comprising the following steps:

1) Enzymatic hydrolysis of oil comprising at least 25% oleic acid using lipase to provide free fatty acids comprising oleic acid, and
2) Hydration of the free fatty acids using oleate hydratase (EC 4.2.1.53), wherein the oleate hydratase is selected from *Stenotrophomonas maltophilia* or derivatives thereof having at least 10% activity when compared with wild-type enzyme under the same conditions or active fragments thereof and/or *Rhodococcus erythropolis* or derivatives thereof having at least 10% activity when compared with wild-type enzyme under the same conditions or active fragments thereof.
3) Separation of 10-HSA in form of a filter cake from the reaction mixture, and
4) Preparation of 10-HSA from the separated filter cake, and wherein, optionally, the lipase and/or the hydratase used in step 1) and/or step 2) is/are recycled and/or immobilised.

Optionally, the enzymatic hydrolysis according to step 1 may also be performed with oil comprising at least 25%, 30%, 35%, 40%, 45%, 50%, 55%, 60%, 65% or 70% oleic acid.

Optionally, the hydration of the free fatty acids using according to step 2 may also be performed with oleate hydratase from *Stenotrophomonas maltophilia* or derivatives thereof having at least 15%, 20%, 30%, 40%, 50%, 60%, 70%, 80%, 90%, 100%, 110%, 120%, 130%, 140%, 150%, 160%. 170%, 180%, 190% or 200% activity when compared with wild-type enzyme under the same conditions or active fragments thereof and/or *Rhodococcus erythropolis* or derivatives thereof having at least 15%, 20%, 30%, 40%, 50%, 60%, 70%, 80%, 90%, 100%, 110%, 120%, 130%, 140%, 150%, 160%. 170%, 180%, 190% or 200% activity when compared with wild-type enzyme under the same conditions or active fragments thereof.

Each value of content of oleic acid of oil according to step 1 may be combined with each value of activity of oleate hydratase or derivatives thereof according to step 2.

According to the present invention it is possible to recycle and/or immobilise the lipase and/or the hydratase used in step 1) and/or step 2), and wherein, optionally, the process according to the present invention may be repeated at least once using the recycled and/or immobilised enzyme(s).

The recycled enzyme(s) may be reused at least twice, preferably 2-100 times, 2-50 times, and most preferably 2-10 or 2-5 times, which is a substantial advantage associated with the process of the present invention.

In one embodiment, said lipase and/or hydratase are immobilised on a carrier, such as a glass, an alginate bead, a matrix, a porous material. In one embodiment, said lipase and/or hydratase are immobilised on the same carrier or on separate carriers.

In one embodiment, the term "derivative" relates to an organism, a molecule, or a substance that is structurally related to another organism, molecule, or substance, respectively, and which is derivable from it, e.g. by mutation or structural modification of said organism, molecule, or substance. In one embodiment, a derivative has similar activity as the organism, molecule, or substance, which the derivative is derived from.

As used herein, the term "cell free" process refers to a process substantially free of intact cells. One of skill in the art would understand that a certain percentage of the cells after lysing may be intact, e.g., less than 10%, less than 5%, less than 2%, less than 1%, or less than 0.5%. A "cell-free system," as used herein, is an isolated cell-free system containing a cell lysate or extract expressly engineered to include an enzyme or cascade of enzymes that, when acting in a given sequence (e.g., in an enzymatic pathway) and proportion over a determined substrate, results in the generation of a desired product (e.g. a biofuel or other chemical compound, or an intermediate thereto).

As used herein, the term "enzymatic" process refers to a reaction which is assisted or catalyzed by an enzyme, herein generally classified as a lipase or hydratase and more specifically identified below. Necessary components for the enzymatic reactions include a substrate.

10-hydroxystearic acid (10-HSA) (CAS: 638-26-6) has the following formula:

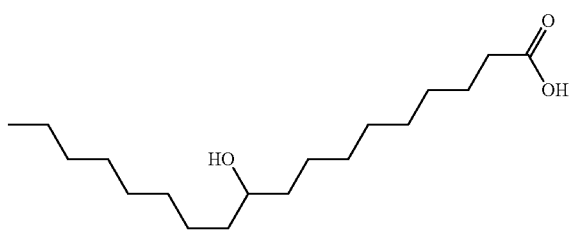 [SMILES: CCCCCCCCC(O)CCCCCCCCC(=O)O]

Both enantiomers may be used according to the present invention.

The term "fatty acid (FA)", as used herein, refers to any carboxylic acid with an aliphatic tail. Most naturally occurring fatty acids have a chain of an even number of carbon atoms, such as from 4 to 28, and are usually derived from triglycerides or phospholipids. Short-chain fatty acids (SCFA) are fatty acids with aliphatic tails of fewer than 6 carbons (e.g., butyric acid). Medium-chain fatty acids (MCFA) are fatty acids with aliphatic tails of 6-12 carbons, which can form medium-chain triglycerides. Long-chain fatty acids (LCFA) are fatty acids with aliphatic tails 12 to 22 carbons. Very long chain fatty acids (VLCFA) are fatty acids with aliphatic tails longer than 22 carbons. FAs can be either unsaturated or saturated.

Unsaturated fatty acids comprise a high percentage of the total fatty acids in plant material consumed by ruminant species. The microbial population that inhabits the rumen transforms dietary unsaturated fatty acids into an array of trans fatty acids, conjugated acids, and stearic acid.

The term "triglyceride", as used herein, refers to an ester derived from glycerol and three fatty acids. There are many different types of triglyceride, with the main division between saturated and unsaturated types. Saturated fats are "saturated" with hydrogen—all available places where hydrogen atoms could be bonded to carbon atoms are occupied. These have a higher melting point and are more likely to be solid at room temperature. Unsaturated fats have double bonds between some of the carbon atoms, reducing the number of places where hydrogen atoms can bond to carbon atoms. These have a lower melting point and are more likely to be liquid at room temperature. Triglycerides are chemically tri esters of fatty acids and glycerol. Triglycerides are formed by combining glycerol with three fatty acid molecules. Alcohols have a hydroxyl (HO—) group. Organic acids have a carboxyl (—COOH) group. The glycerol molecule has three hydroxyl (HO—) groups. Each fatty acid has a carboxyl group (—COOH). In triglycerides, the hydroxyl groups of the glycerol join the carboxyl groups of the fatty acid to form ester bonds:

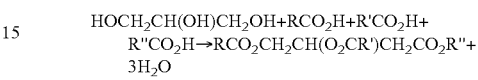

$$R''CO_2H \rightarrow RCO_2CH_2CH(O_2CR')CH_2CO_2R''+ 3H_2O$$

The three fatty acids ($RCO_2H$, $R'CO_2H$, $R''CO_2H$ in the above equation) are usually different, but many kinds of triglycerides are known. The chain lengths of the fatty acids in naturally occurring triglycerides vary, but most contain 16, 18, or 20 carbon atoms. Natural fatty acids found in plants and animals are typically composed of only even numbers of carbon atoms, reflecting the pathway for their biosynthesis from the two-carbon building-block acetyl CoA. Bacteria, however, possess the ability to synthesize odd- and branched-chain fatty acids. As a result, ruminant animal fat contains odd-numbered fatty acids, such as 15, due to the action of bacteria in the rumen. Many fatty acids are unsaturated, some are polyunsaturated (e.g., those derived from linoleic acid). Most natural fats contain a complex mixture of individual triglycerides.

As used herein, the term "enzymatic hydrolysis" relates to a process in which enzymes facilitate the cleavage of bonds in molecules with the addition of the elements of water.

Fats and oils are hydrolyzed by moisture to yield glycerol and 3 fatty acids. Chemically fats are esters, so they are liable to hydrolysis. This reaction is catalyzed by a lipase or can occur via non-enzymatic hydrolysis. Partial hydrolysis of triglycerides will yield mono- and di-glycerides and free fatty acids. When hydrolysis is carried to completion with water in the presence of an acid catalyst, the mono-, di-, and triglycerides will hydrolyzed to yield glycerol and free fatty acids. Enzyme reactions require milder conditions, less solvent, and give cleaner products attributes of green chemistry. There is increasing interest in the use of lipase enzymes for large-scale reactions. Reaction generally occurs under milder conditions of temperature and pH and there is reduced danger of undesirable side-reactions.

Oleic acid, as used herein, is a fatty acid that occurs naturally in various animal and vegetable fats and oils. It is an odorless, colorless oil, though commercial samples may be yellowish. In chemical terms, oleic acid is classified as a monounsaturated omega-9 fatty acid, abbreviated with a lipid number of 18:1 cis-9. It has the formula $CH_3(CH_2)_7 CH{=}CH(CH_2)_7COOH$. The term "oleic" means related to, or derived from, olive oil which is mostly composed of oleic acid.

The term "triglyceride lipase" as used herein, relates to lipases that hydrolyse ester linkages of triglycerides. These lipases are widely distributed in animals, plants and prokaryotes. This family was also called class 3 lipases as they are only distantly related to other lipase families. In particular, the triglyceride lipase EC class 3.1.1.3 ("triacylglycerol lipase"), as used herein, relates to the pancreatic enzyme that acts only on an ester-water interface, wherein the outer ester links are preferentially hydrolysed. The triacylglycerol lipase (EC 3.1.1.3, lipase) catalyses the following chemical reaction: triacylglycerol+H$_2$O diacylglycerol+a carboxylate.

As used herein, the term "hydration" relates to a chemical process that introduces a hydroxyl group (—OH) into an organic compound. Hydratases are a group of lyases that catalyze hydration and dehydration of a substrate. Even though many hydratases are known, yet there are only few known oleate hydratases[6]. Oleate hydratases belong to the group of fatty acid hydratases and convert oleic acid into (R)-10-hydroxystearic acid (EC 4.2.1.53).

Hydratases (EC 4.2.1.53), as used herein, catalyze the regio-specific, irreversible addition of a hydrogen atom and a hydroxy group from water to the carbon-carbon cis-double bond of unsaturated fatty acids at the C9 and C10 positions, respectively, to make 10-hydroxy fatty acids (Joo et al., 2012a). Oleate hydratases convert oleic acid to 10-hydroxystearic acid as shown in Scheme 1:

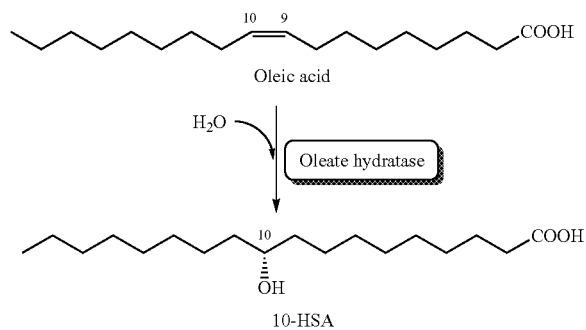

Oleate Hydratase Homologies:

As used herein, "oleate hydratases" have sequence identities of oleate hydratase enzymes from different taxonomic origins are displayed in FIGS. 1 and 2. With any enzyme of this family the hydration of oleic acid can be carried out with different degrees of efficiency.

In some embodiments, reactions are carried out with a native oleate hydratase, one or several of such oleate hydratases, or respective mutants thereof (with a sequence identity of more than 80% and functional for the described application), selected from *Stenotrophomonas maltophilia* (Sma), *Elizabethkingia meningoseptica* (ohyA), *Macrococcus caseolyticus* (Mca), *Bifidobacterium breve* (Bbr), *Corynebacterium kroppenstedtii* (Ckr), *Ochrobactrum anthropi* (Oan), *Myroides odoratus* (Mod), *Staphylococcus aureus* (Sau), *Chryseobacterium gleum* (Cgl), *Cellulophaga algicola* (Cal), *Rhodococcus erythropulus* (Rre) and *Lactobacillus acidophilus* (Lac).

In further embodiments, reactions are carried out with one or several oleate hydratases selected from *Stenotrophomonas maltophilia* (Sma), *Elizabethkingia meningoseptica* (ohyA) and *Rhodococcus erythropulus* (Rre), or with respective mutants thereof.

In further embodiments, reactions are carried out with one or several oleate hydratases from *Stenotrophomonas maltophilia* (Sma) or mutants or derivatives thereof and/or *Rhodococcus erythropulus* (Rre) or with respective mutants or derivatives thereof.

In additional embodiments, the reaction is carried out with the oleae hydratase from *Stenotrophomonas maltophilia* (Sma, gene Smlt2093) published by Joo et al.[7].

In another embodiment of the present application, the specificity of the hydration of oleic acid with the oleate hydratase from *Stenotrophomonas maltophilia* can be detected using GC-MS chromatography (FIG. 3; RT 22.72: C12:0; RT 32.80: palmitic acid; RT 37.26: stearic acid; RT 37.76: oleic acid; RT 38.62: linoleic acid; RT 48.67: 10-hydroxystearic acid (10-HSA)). The direct transesterification of the hydration reaction products was performed according to a modified protocol of Griffiths et al.[8] with the following modifications: replacement of the C17-TAG by a C12-TAG, replacement of BF3 methanol by a HCL-methanol solution, and the C19-ME was omitted. Subsequently, the resulting fatty acid methyl ester (FAME) extract was injected into a Thermo Scientific™ TRACE™ Ultra Gas Chromatograph coupled to a Thermo DSQ™ II mass spectrometer and the Triplus™ Autosampler injector. Column: Stabilwax® fused silica capillary (30 m×0.25 mm, film thickness 0.25 m). (Program: initial column temperature 50° C., increasing (4° C./min) up to a final temperature of 250° C. Carrier gas: hydrogen, flow rate 3.5 mL/min.) Peaks were identified by comparison to a marine oil standard (Restek) or by specific molecular masses detected. The GC-MS chromatogram shows a high conversion level from OA to 10-HSA by the oleate hydratase from *S. maltophilia*. This high conversion level is achieved, although the converted substrate was containing contaminants, like palmitic acid, that were reported to decrease the conversion efficiency of the oleate hydratase reaction.[5a] These results demonstrate, that an efficient hydration reaction can be carried out with the oleate hydratase from *S. maltophilia*, even if the utilized substrate in not only pure OA.

In another embodiment of the present application, the specificity of the hydration of oleic acid with the oleate hydratase from *Rhodococcus erythropulus* can be detected using GC-FID chromatography (FIG. 4, RT 7.5: oleic acid; RT 15.6: 10-hydroxystearic acid (10-HSA)). The preparation of the extracted lipid fractions for the GC measurements was performed according to Volkov et al.[9] Extracts were analyzed with the Shimadzu™ GC-2025 system equipped with a flame ionization detector. Column: Zebron ZB-WAX (30 m×0.32 mm, film thickness 0.25 µm) Phenomenex. Carrier gas: hydrogen (3.00 ml/min). Program: initial column temperature 150° C. for 1 min; increasing 5° C./min to 240° C., hold for 6 min. Peaks were identified by comparison to the respective standards or previous GC-MS results. The results depicted in FIG. 4 demonstrate the efficient conversion of pure OA to 10-HSA by the oleate hydratase from *R. erythropolis*. Approximately 95% of the applied substrate is converted within 15 min under the given conditions.

A further embodiment of the present invention is the process according to the preceding embodiments, wherein said oil in step 1 is selected from the group comprising renewable/regrowing feedstocks (of bio-based oils).

The term(s) "renewable" or "regrowing", as used herein, means that something is capable of being renewed or is a substance of economic value that can be replaced or replenished in the same or less amount of time as it takes to draw the supply down. Some renewable resources are considered renewable even though some time or effort must go into their renewal.

As used herein, the term "feedstocks" refers to raw materials (input) fed into a process for conversion into something different (output). For example, crude oil is a feedstock raw material providing finished products in the fuel, plastic, industrial chemical and pharmaceutical industries. The term "raw material" is used to denote material is in an unprocessed or minimally processed state.

In another embodiment the present invention relates to the process as defined in any one of the preceding embodiments, wherein said feedstocks are selected from the group comprising animals, plants and microorganisms.

In another embodiment the present application relates to the process as defined in any one of the preceding embodiments, wherein said oil comprises mono-, di- or triglycerides.

In another embodiment the present application relates to the process as defined in any one of the preceding embodiments, wherein said oil comprises triglycerids with an oleic acid content ≥40%.

In another embodiment the present application relates to the process as defined in any one of the preceding embodiments, wherein said oil comprises triglycerids with an oleic acid content ≥50%.

In another embodiment the present application relates to the process as defined in any one of the preceding embodiments, wherein said oil comprises triglycerids with an oleic acid content ≥70%.

In another embodiment the present application relates to the process as defined in any one of the preceding embodiments, wherein said oil is a plant oil selected from the group comprising, preferably consisting of vegetable oil, tree borne oil, olive oil, mustard oil, linseed oil, canola oil, coconut oil, coriander oil, corn oil, cottonseed oil, hazelnut oil, olive oil, neem oil, palm oil, peanut oil, rapeseed oil, rice bran oil, safflower oil, soybean oil, sunflower seed oil, and mixtures thereof.

In another embodiment the present application relates to the process as defined in any one of the preceding embodiments, wherein said oil is an animal oil selected from the group comprising, preferably consisting of tall, fish and crustacean oils.

In another embodiment the present application relates to the process as defined in any one of the preceding embodiments, wherein said oil is a microbial oil.

In another embodiment the present application relates to the process as defined in any one of the preceding embodiments, wherein said oil is derived from bacteria, yeast, algae and/or fungi.

In another embodiment the present application relates to the process as defined in any one of the preceding embodiments, wherein said oil is a microbial oil from oleganious yeast, algae and molds. Examples are oils from *Nannochloropsis salina* (algae), *Rhodospirillum tourolides* (bacteria), *Trichosporon oleganosus* (fungus), *Yarrowia lipolytica* (yeast).

In another embodiment the present application relates to the process as defined in any one of the preceding embodiments, wherein said lipase is selected from the group comprising, preferably consisting of mono-, di- or triglyceride lipase.

In another embodiment the present application relates to the process as defined in any one of the preceding embodiments, wherein said lipase is a lipase selected from the EC class of hydrolases (EC class 3), preferably from the EC class of esterase enzymes acting on ester bonds (EC class 3.1), more preferably from the class of carboxylic-ester hydrolases (EC class 3.1.1).

In another embodiment the present application relates to the process as defined in any one of the preceding embodiments, wherein said lipase is a lipase selected from the EC class of triglyceride lipases (EC class 3.1.1.3).

In another embodiment the present application relates to the process as defined in any one of the preceding embodiments, wherein said lipase is a triglyceride lipase selected from the group comprising, preferably consisting of *Candida rugosa* lipase, or lipase from porcine pancreas, lipase from *Rhizopus oryzae* or lipase from *Pseudomonas* sp.

In another embodiment the present application relates to the process as defined in any one of the preceding embodiments, wherein said enzymatic hydrolysis using lipase is carried out in the presence of a catalyst.

As used herein, the term "catalyst" refers to a substance that speeds up a chemical reaction, but is not consumed by the reaction; hence a catalyst can be recovered chemically unchanged at the end of the reaction it has been used to speed up, or catalyze.

In another embodiment the present application relates to the process as defined in any one of the preceding embodiments, wherein said catalyst is selected from the group comprising Tween®, Tween-20® or ethanol.

In another embodiment the present application relates to the process as defined in any one of the preceding embodiments, wherein said enzymatic hydrolysis is carried out in an aqueous system.

As used herein, the term "aqueous system" comprises an aqueous solution that is any solution in which water ($H_2O$) is the solvent.

In another embodiment the present application relates to the process as defined in any one of the preceding embodiments, wherein said aqueous system comprises at least one buffer and/or at least one solvent, mixtures of solvents and/or mixtures of buffer(s) and solvent(s).

In another embodiment the present application relates to the process as defined in any one of the preceding embodiments, wherein said buffer is selected from Tris-HCl buffer, phosphate-citrate-buffer, 3-(N-morpholino)propanesulfonic acid (MOPS) buffer.

In another embodiment the present application relates to the process as defined in any one of the preceding embodiments, wherein the concentration of said buffer is in the range of 10 mM to 100 mM, preferably 10 mM to 50 mM, more preferably 15 mM to 40 mM, most preferably 20 mM to 30 mM.

In another embodiment the present application relates to the process as defined in any one of the preceding embodiments, wherein the concentration of said buffer is 20 mM+5%.

In another embodiment the present application relates to the process as defined in any one of the preceding embodiments, wherein the *Candida rugosa* lipase is used in 20 mM Tris-HCl buffer with a pH value of 7.2.

In another embodiment the present application relates to the process as defined in any one of the preceding embodiments, wherein said enzymatic hydrolysis is carried out at a temperature ranging from 10° C. to 60° C.

In another embodiment the present application relates to the process as defined in any one of the preceding embodiments, wherein said enzymatic hydrolysis is carried out at a temperature ranging from 20° C. to 50° C.

In another embodiment the present application relates to the process as defined in any one of the preceding embodiments, wherein said enzymatic hydrolysis is carried out at a temperature ranging from 30° C. to 40° C.

In another embodiment the present application relates to the process as defined in any one of the preceding embodiments, wherein said enzymatic hydrolysis is carried out at a temperature of 37° C.+5%.

In another embodiment the present application relates to the process as defined in any one of the preceding embodiments, wherein said enzymatic hydrolysis is carried out for a period of 15 to 300 minutes, preferably 30 to 180 minutes, more preferably 60-90 min.

In another embodiment the present application relates to the process as defined in any one of the preceding embodiments, wherein after the enzymatic hydrolysis, glycerol is separated from the free fatty acids in a washing step using water/buffer and/or by extracting the free fatty acids from the reaction mixture using at least one organic solvent and/or by phase separation.

As used herein, the term "extraction" relates to a way to separate a desired substance when it is mixed with others. The mixture is brought into contact with a solvent in which the substance of interest is soluble, but the other substances present are insoluble. Extractions use two immiscible phases (these are phases that do not mix, like oil and water) to separate the substance from one phase into the other.

In one embodiment the present application relates to the process as defined in any one of the preceding embodiments, wherein said enzymatic hydrolysis of oil using lipase (step 1) and the hydration using oleate hydratase (step 2) can be carried out, preferably are carried out sequentially or simultaneously (see Scheme 2, Process option I or II).

In another embodiment, the present application relates to the process as defined in any one of the preceding embodiments, wherein said enzymatic hydrolysis of oil using lipase (step 1) and the hydration using oleate hydratase (step 2) can be carried out, preferably are carried out together or concurrently.

In one embodiment the present application relates to the process as defined in any one of the preceding embodiments, wherein in a first step the enzymatic hydrolysis of oil using lipase is performed. Following this reaction, a washing/purification step is carried out, wherein the free fatty acids (e.g. oleic acid) are separated from the residual reaction mixture.

As used herein, the term "purification" in chemistry relates to a separation of a substance into its components and refers to the process of removing impurities.

As used herein, the term "separation" relates to a process to achieve any phenomenon that converts a mixture of chemical substance into two or more distinct product mixtures, which may be referred to as mixture, at least one of which is enriched in one or more of the mixture's constituents. In some cases, a separation may fully divide the mixture into its pure constituents. Separations differ in chemical properties or physical properties such as size, shape, mass, density, or chemical affinity, between the constituents of a mixture. They are often classified according to the particular differences they use to achieve separation. Usually there is only physical movement and no substantial chemical modification. If no single difference can be used to accomplish a desired separation, multiple operations will often be performed in combination to achieve the desired end.

The term "together or concurrently", as used herein in the context of the performance of two reaction steps, is meant to refer to a scenario, wherein the two steps are performed without any deliberate separation between them, neither temporally nor spatially. To achieve this, in a preferred embodiment, the two reaction steps are carried out such that the oil is exposed to both lipase and oleate hydratase at the same time together. In one embodiment, the oil is exposed to both the lipase and the hydratase in the same reaction vessel. This is herein also sometimes referred to as one-pot synthesis.

In another embodiment the present application relates to the process as defined in any one of the preceding embodiments, wherein in a first step (step 1) the enzymatic hydrolysis of oil using lipase is performed resulting in a mixture of buffer, enzyme, glycerin, oleic acid or a mixture of free fatty acids (FFAs) comprising oleic acid, wherein the main component of the free fatty acids is oleic acid. Subsequently, water and glycerin are separated from the free fatty acids (FFAs) which are dissolved in at least one organic solvent. The end product, the FFAs, is obtained by removal of the organic solvent(s), wherein said solvent can be used for another wash/purification step.

In another embodiment the present application relates to the process as defined in any one of the preceding embodiments, wherein in a second step (step 2) the enzymatic hydration of oleic acid using oleate hydratase is performed resulting in a mixture of buffer, enzyme, residual amounts of oleic acid, for example, ≤10%, ≤7.5, ≤5%, or even below, and 10-HSA. Subsequently, the precipitated 10-HSA is separated as a filter cake containing 10-HSA and the remaining ingredients of the reaction mixture comprising buffer and enzyme are recycled for a new reaction (see scheme 2, Process option I).

In one embodiment, said first step and said second step are performed together or concurrently, preferably in a single reaction vessel. This is also sometimes herein referred to as "one-pot synthesis".

The term "filter cake", as used herein, is formed by the substances that are retained on a filter. The filter cake grows in the course of filtration, becomes "thicker" as particulate matter is being retained. With increasing layer thickness the flow resistance of the filter cake increases. After a certain time of use the filter cake has to be removed from the filter, e.g. by backflushing. If this is not accomplished, the filtration is disrupted because the viscosity of the filter cake gets too high, thus too little of the mixture to be filtered can pass through the filter cake and the filter plugs. The specifications of the filter cake dictate the filtration method of choice.

In another embodiment the present application relates to the process as defined in any one of the preceding embodiments, wherein the enzymatic hydrolysis of oil using lipase and the hydration using oleate hydratase is performed simultaneously. Following this reaction, the product, 10-HSA, is separated from the reaction mixture (using filtration) and the remaining ingredients of the reaction mixture are recycled for a new reaction.

In another embodiment the present application relates to the process as defined in any one of the preceding embodiments, wherein the enzymatic hydrolysis of oil using lipase and the hydration using oleate hydratase are performed together or concurrently, wherein said enzymatic hydrolysis of oil using lipase and said hydration using oleate hydratase are preferably performed in a single reaction vessel. This is herein also sometimes referred to as a one-pot synthesis. In one embodiment, said one-pot synthesis allows for higher efficiency and faster synthesis of 10-HSA compared to a production of 10-HSA which is not performed as a one-pot synthesis. In one embodiment, said one-pot synthesis is performed using a lipase and/or a hydratase which is/are immobilised on a carrier. In one embodiment, said one-pot synthesis is performed using a lipase and a hydratase which are immobilised on a carrier, wherein said lipase and said hydratase are immobilised on the same carrier or on separate carriers.

In another embodiment the present application relates to the process as defined in any one of the preceding embodiments, wherein said enzymatic hydrolysis of oil using lipase (step 1) and the hydration using oleate hydratase (step 2) is performed simultaneously, and subsequently, the precipitated product, 10-HSA, is separated from the reaction mixture comprising buffer, enzymes, glycerin and oleic acid using filtration. The precipitated 10-HSA is thereby separated as a filter cake and the remaining ingredients of the reaction mixture are recycled for a new reaction (see scheme 2 in FIG. 19, Process option II).

In another embodiment the present application relates to the process as defined in any one of the preceding embodiments, wherein the purification of 10-HSA comprises the following steps: a) an extraction with at least one organic solvent, and b) a phase separation.

In another embodiment the present application relates to the process as defined in any one of the preceding embodiments, wherein the purification of 10-HSA comprises an extraction with at least one organic solvent, wherein a mixture of 10-HSA, organic solvent, buffer, and enzymes are extracted from the filter cake containing 10-HSA. Subsequently, 10-HSA which is dissolved in at least one organic solvent is separated by phase separation from a waste fraction comprising residual water and denatured enzymes. The end product 10-HSA is obtained by removing the organic solvent(s), wherein said solvent(s) can be reused for the extraction from the filter cake (see scheme 2 in FIG. 19, box on the right).

In another embodiment the present application relates to the process as defined in any one of the preceding embodiments, wherein after the enzymatic hydrolysis (step 1) said free fatty acids are optionally separated from the reaction mixture by at least one washing/purification step.

In another embodiment the present application relates to the process as defined in any one of the preceding embodiments, wherein after the enzymatic hydrolysis (step 1), said free fatty acids are separated from glycerol in at least one washing/purification step by extraction or phase separation.

In another embodiment the present application relates to the process as defined in any one of the preceding embodiments, wherein after the enzymatic hydrolysis (step 1) said free fatty acids are optionally separated from the reaction mixture by at least one washing/purification step using at least one organic solvent and/or an aqueous system.

In another embodiment the present application relates to the process as defined in any one of the preceding embodiments, wherein said organic solvent for the washing/purification of the free fatty acids is selected from the group comprising ethyl acetate, hexane, toluene, methyl isobutyl ketone (MIBK), methanol, ether.

In another embodiment the present application relates to the process as defined in any one of the preceding embodiments, wherein said organic solvent is ethyl acetate.

In another embodiment the present application relates to the process as defined in any one of the preceding embodiments, wherein said organic solvent for the washing/purification of the free fatty acids is used in an amount which corresponds to the solubility of the free fatty acids or 10-HSA in the solvent, respectively.

In another embodiment the present application relates to the process as defined in any one of the preceding embodiments, wherein said hydration using oleate-hydratase (step 2) is carried out in an aqueous system.

In another embodiment the present application relates to the process as defined in any one of the preceding embodiments, wherein said aqueous system for the hydration comprises buffer, free fatty acids as substrate, oleate hydratase and/or emulsifier.

In another embodiment the present application relates to the process as defined in any one of the preceding embodiments, wherein said emulsifier is selected from the group comprising Tween®, Tween-20® or ethanol.

In another embodiment the present application relates to the process as defined in any one of the preceding embodiments, wherein said hydration is carried out in a buffer selected from the group comprising Tris-HCl buffer, phosphate-citrate-buffer, 3-(N-morpholino)propanesulfonic acid (MOPS) buffer, 2-(N-morpholino)ethanesulfonic acid (MES) buffer, piperazine-N,N'-bis(2-ethanesulfonic acid) (PIPES); 4-(2-hydroxyethyl)-1-piperazineethanesulfonic acid (HEPES); Sorensen's phosphate buffer (Stock solutions: A 0.2 M $NaH_2PO_4$, B 0.2 M $Na_2HPO_4$).

In another embodiment the present application relates to the process as defined in any one of the preceding embodiments, wherein the hydration using oleate hydratase from ohySm is carried out in 50 mM phosphate-citrate-buffer with a pH value of 6.5.

In another embodiment the present application relates to the process as defined in any one of the preceding embodiments, wherein said hydration is carried out at a temperature ranging from 10° C. to 50° C., preferably 20-40° C., more preferably 25-35%.

In another embodiment the present application relates to the process as defined in any one of the preceding embodiments, wherein said hydration results in at least 25, 50, 75, 100%, or more conversion of said fatty acids (comprising oleic acid) to 10-HSA.

In another embodiment the present application relates to the process as defined in any one of the preceding embodiments, wherein said hydration is carried out for a period of 10 to 300 minutes, preferably 30 to 180 minutes, more preferably 60 to 90 minutes.

In another embodiment the present application relates to the process as defined in any one of the preceding embodiments, wherein the hydration is carried out under constant mixing, wherein the speed is in the range of 250 und 750 rpm.

In another embodiment the present application relates to the process as defined in any one of the preceding embodiments, wherein the product of the hydration (step 2), 10-HSA may form flocks that can be separated from the mixture by filtration, precipitation, sedimentation or gravimetric solid-liquid-separation.

The term flocculation, as used herein, is a process wherein colloids come out of suspension in the form of flock or flake, either spontaneously or due to the addition of a clarifying agent. The action differs from precipitation in that, prior to flocculation, colloids are merely suspended in a liquid and not actually dissolved in a solution. In the flocculated system, there is no formation of a cake, since all the flocks are in the suspension.

Optionally, it is possible to add a flocculation agent.

In another embodiment the present application relates to the process as defined in any one of the preceding embodiments, wherein the size of the flocks is further dependent on the pH value of the reaction mixture.

In another embodiment the present application relates to the process as defined in any one of the preceding embodiments, wherein said flocks preferably tend to form in an alkaline pH range.

In another embodiment the present application relates to the process as defined in any one of the preceding embodiments, wherein said pH value is in a range from 5-10.

In another embodiment the present application relates to the process as defined in any one of the preceding embodiments, wherein said pH value is in a range from 5-8.

In another embodiment the present application relates to the process as defined in any one of the preceding embodiments, wherein an emulsion breaker is used additionally to improve the formation of flocks.

In another embodiment the present application relates to the process as defined in any one of the preceding embodiments, wherein after the hydration (step 2) the precipitated 10-HSA is separated from the reaction mixture as filter cake.

In another embodiment the present application relates to the process as defined in any one of the preceding embodiments, wherein said filter cake comprises 10-HSA.

In another embodiment the present application relates to the process as defined in any one of the preceding embodiments, wherein after the hydration (step 2) the precipitated 10-HSA is separated from the reaction mixture as filter cake using filtration and/or centrifugation and/or using chromatographic methods.

In another embodiment the present application relates to the process as defined in any one of the preceding embodiments, wherein after the hydration product, 10-HSA, is optionally separated from the reaction mixture as filter cake by at least one filtration step using a filter.

In another embodiment the present application relates to the process as defined in any one of the preceding embodiments, wherein after the hydration product, 10-HSA, is optionally separated from the reaction mixture using chromatographic methods, for example, by hydrophobic adsorber packed in a column.

In another embodiment the present application relates to the process as defined in any one of the preceding embodiments, wherein after the hydration (step 2) the precipitated 10-HSA is separated from the reaction mixture as filter cake by at least one filtration step using a plate filter press.

In another embodiment the present application relates to the process as defined in any one of the preceding embodiments, wherein said filter is selected from the group comprising a deep bed filter, fabric with pores of a size up to 30 µm, miracloth (rayon-polyester+acrylic binder), cellulose filter with pores of a size up to 30 µm.

In another embodiment the present application relates to the process as defined in any one of the preceding embodiments, wherein after the hydration (step 2), 10-HSA is prepared from the filter cake using extraction with at least one organic solvent and/or using phase generation.

In another embodiment the present application relates to the process as defined in any one of the preceding embodiments, wherein after the hydration (step 2), 10-HSA is prepared from the filter cake using extraction with at least one organic solvent, wherein the 10-HSA is dissolved in the at least one organic solvent and afterwards the organic phase is separated from the denatured protein and the residual water.

In another embodiment the present application relates to the process as defined in any one of the preceding embodiments, wherein after the hydration (step 2), 10-HSA is prepared from the filter cake using extraction with at least one organic solvent, wherein water is added prior extraction in order to improve the formation of delimited phases.

In another embodiment the present application relates to the process as defined in any one of the preceding embodiments, wherein after the hydration (step 2), 10-HSA is prepared from the filter cake using extraction with at least one organic solvent, wherein said organic solvent is selected from the group comprising ethyl acetate, hexane, methanol, ether, methyl-isobutyl-ketone, toluene.

In another embodiment the present application relates to the process as defined in any one of the preceding embodiments, wherein the concentration of said organic solvent is between 80% w/v to 100% w/v.

In another embodiment the present application relates to the process as defined in any one of the preceding embodiments, wherein the concentration of said organic solvent is ≤90% w/v.

In another embodiment the present application relates to the process as defined in any one of the preceding embodiments, wherein after the extraction of 10-HSA from the filter cake, an isolation/purification of 10-HSA is performed (step 4) using phase separation.

In another embodiment the present application relates to the process as defined in any one of the preceding embodiments, wherein said purification of 10-HSA from the filter cake (step 4) is performed by phase separation, wherein the dissolved 10-HSA is separated from the residual fraction/reaction mixture comprising water and enzymes.

In another embodiment the present application relates to the process as defined in any one of the preceding embodiments, wherein said purification of 10-HSA from the filter cake (step 4) is performed by phase separation, wherein 10-HSA is dissolved in at least one organic solvent. The extraction of 10-HSA with at least one organic solvent, as used herein, facilitates a separation of the product from other contaminants (e.g. catalysts, buffer salts etc.).

In another embodiment the present application relates to the process as defined in any one of the preceding embodiments, wherein said organic solvent for the extraction of 10-HSA is selected from the group comprising ethyl acetate, hexane, methanol, ether, methyl-isobutyl-ketone, toluene.

In another embodiment the present application relates to the process as defined in any one of the preceding embodiments, wherein the concentration of said organic solvent is between 80% w/v to 100% w/v.

In another embodiment the present application relates to the process as defined in any one of the preceding embodiments, wherein the concentration of said organic solvent is ≤90% w/v.

In another embodiment the present application relates to the process as defined in any one of the preceding embodiments, wherein the organic solvent is removed by evaporation, distilling, gassing with nitrogen and/or phase separation.

In one embodiment the present application relates to the process as defined in any one of the preceding embodiments, further comprising preparing a composition or product preferably selected from speciality oleochemicals, chemical performance additives, cosmetics, cosmetic additives, in particular lubricants. In one embodiment the present application relates to the process as defined in any one of the preceding embodiments, wherein 10-HSA prepared by said process is subsequently lactonised. In one embodiment, said lactonising is performed using a microorganism such as *Saccharomyces cerevisiae, Debaromyces hansenii, Candida boidinii, Candida silvicola, Candida apicola, Zygosaccharomyces fermentati*, or *Torulaspora delbruckii*. In one embodiment the present application relates to the process as defined in any one of the preceding embodiments, further comprising lactonising 10-HSA prepared by said process, and preparing a composition or product preferably selected from fragrances, odorants, and aroma compounds. In another embodiment the present application relates to a composition or product comprising 10-HSA obtainable by the process according to any of the preceding embodiments. In one embodiment, said composition or product is selected from specialty oleochemicals, chemical performance additives, cosmetics, cosmetic additives, in particular lubricants. In one embodiment, said composition or product comprising 10-HSA obtainable by the process according to any of the preceding embodiments is used as a specialty oleochemical, chemical performance additive, cosmetic, or cosmetic additive, in particular as a lubricant. In one embodiment, said 10-HSA obtainable, preferably obtained, by the process according to any of the preceding embodiments is lactonised, and the resulting lactonised product is used as a fragrance, an odorant, or an aroma compound.

EXAMPLES/EXPERIMENTS

1.) Hydrolysis of High Oleic Sunflower Oil (HOSO), as an Example for a Bio-Based Oil The conventional lipase based hydrolysis of bio-based oil is known to those skilled in the art (Enzymatic process for fat and oil hydrolysis, WO 2013114178 A1). More specifically, the hydrolysis of the HOSO, consisting of over 90% triolein, is carried out by a lipase (EC 3.1.1.3). An appropriate catalyst is chosen and the reaction is carried out under its corresponding conditions. After the lipolytic cleavage of the triolein the glycerol is separated from the FFAs by either an additional washing step with water/buffer or by extracting the FFAs from the reaction mixture with an organic solvent. Alternative extraction methods for free fatty acids, such as distillation are known to those skilled in the art.

Scheme 3: Reaction scheme of lipase catalyzed hydrolysis of triolein

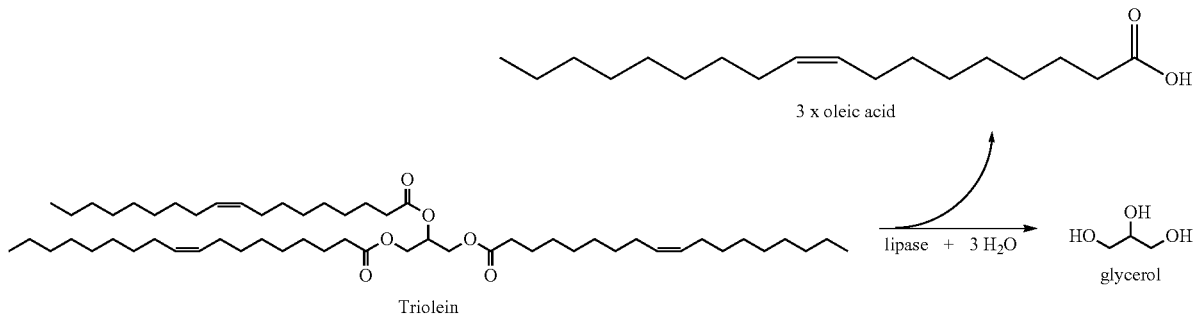

REFERENCES

[1] L. L. Wallen, R. G. Benedict, R. W. Jackson, *Archives of Biochemistry and Biophysics* 1962, 99, 205-357.

[2] L. E. Bevers, M. W. Pinkse, P. D. Verhaert, W. R. Hagen, *J Bacteriol* 2009, 191, 5010-5012.

[3] M. Engleder, T. Pavkov-Keller, A. Emmerstorfer, A. Hromic, S. Schrempf, G. Steinkellner, T. Wriessnegger, E. Leitner, G. A. Strohmeier, I. Kaluzna, D. Mink, M. Schurmann, S. Wallner, P. Macheroux, K. Gruber, H. Pichler, *Chembiochem* 2015, 16, 1730-1734.

[4] A. Volkov, S. Khoshnevis, P. Neumann, C. Herrfurth, D. Wohlwend, R. Ficner, I. Feussner, *Acta Crystallogr D Biol Crystallogr* 2013, 69, 648-657.

[5] aB. N. Kim, Y. C. Joo, Y. S. Kim, K. R. Kim, D. K. Oh, *Appl Microbiol Biotechnol* 2012, 95, 929-937; bW. R. Kang, M. J. Seo, K. C. Shin, J. B. Park, D. K. Oh, *Biotechnol Bioeng* 2017, 114, 74-82.

[6] A. Hiseni, I. W. C. E. Arends, L. G. Otten, *Chemcatchem* 2015, 7, 29-37.

[7] Y. C. Joo, E. S. Seo, Y. S. Kim, K. R. Kim, J. B. Park, D. K. Oh, *J Biotechnol* 2012, 158, 17-23.

[8] M. J. Griffiths, R. P. van Hille, S. T. Harrison, *Lipids* 2010, 45, 1053-1060.

[9] A. Volkov, A. Liavonchanka, O. Kamneva, T. Fiedler, C. Goebel, B. Kreikemeyer, I. Feussner, *J Biol Chem* 2010, 285, 10353-10361.

Commercially available lipase from *Candida rugosa* is used to hydrolyze HOSO under mild conditions in an aqueous reaction system (10 mg/ml lipase; 20 mM HOSO; 20 mM Tris-HCl buffer pH 7.2). After the reaction, the produced glycerol is removed by a washing step with water and the FFAs are extracted from the reaction mixture by the addition of ethyl acetate and a subsequent separation of the organic and aqueous phase. The organic solvent is removed by evaporation or gassing with nitrogen. The obtained FFAs are used for following experiments.

2.) Oleate Hydratase Catalyzed Hydration of Oleic Acid

The second step in the process from bio-based oils to 10-HSA is the addition of a hydroxyl group to the carbon chain of the unsaturated FA, which is carried out by an oleate hydratase (EC 4.2.2.53). An appropriate catalyst is chosen and the reaction is carried out under its corresponding conditions. After the addition of the hydroxyl group to the fatty acid chain the product is separated from the reaction mixture by one of the following methods.

The first method is the direct exposure of the reaction mixture to an organic solvent, e.g. ethyl acetate, in an adequate volume. The produced aqueous and organic phases are subsequently separated and the organic solvent is removed by evaporation, or recovered by distilling. After the removal of the organic solvent, the 10-HSA appears as a crystalline, white wax.

In an adjacent step the product is separated by a filtering step before the addition of an organic solvent. The additional filtering step reduces the amount of organic solvent for the extraction and allows a partial recovery of the enzyme solution applied for the hydration reaction. The concentration of the product from the reaction mixture can be performed by different filtering methods. The first option is the usage of a suitable deep bed filter. The second option is the usage of a suitable fabric with small pores of a size up to 30 µm. These filtering methods reduce the volume to be extracted by the organic solvent by approximately 90%. The resulting filter cake is then extracted as described in the first method. The resulting filtrate was shown to exhibit enough recycled, active enzyme to perform multiple hydration steps.

Scheme 4: Reaction scheme of the hydration of oleic acid to 10-hydroxystearic acid by an oleate hydratase.

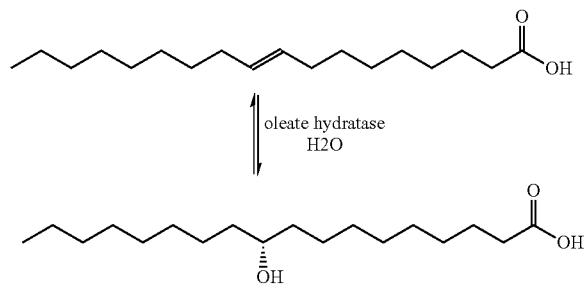

3.) Hydration of FFAs Using Oleate Hydratase from *Stenotrophomonas maltophilia* (Strain K279a)

The gene Smlt2093, coding for a putative myosin-cross-reactive antigen, from *Stenotrophomonas maltophilia* (strain K279a), was taken as a template for a codon-optimized gene-synthesis (life-technologies), for an *E. coli* host strain. The obtained synthetic gene was sub-cloned in a pET28a expression plasmid and transformed into chemically competent *E. coli* BL21DE3 cells. The oleate hydratase is heterologously expressed in *E. coli* BL21DE3 cells, grown in Laure Broth (LB) medium. After an appropriate time of protein expression, cells are harvested from the culture and disrupted by high pressure homogenization. The cell-debris is separated from the oleate hydratase containing liquid phase and discarded.

The resulting lysate is then used for the hydration of the FFAs-fraction from step 1). The reaction is carried out, as described by Joo et al.[7], in an aqueous system at low temperatures under constant mixing. After an appropriate reaction time the product (10-HSA) can be separated from the reaction mixture by one of the methods described above.

4.) Hydration of FFAs Using Oleate Hydratase from *Rhodococcus erythropolis* CCM2595

The myosin-cross-reactive antigen coding gene 05Y_00450 from *Rhodococcus erythropolis* CCM2595, was taken as a template for a codon-optimized gene-synthesis (life-technologies), for an *E. coli* host strain. The obtained synthetic gene was sub-cloned in a pET28a expression plasmid and transformed into chemically competent *E. coli* BL21DE3 cells. The native oleate hydratase or respective mutants thereof are expressed in *E. coli* BL21DE3 cells, grown in Laure Broth (LB) medium. After an appropriate time of protein expression, cells are harvested from the culture and disrupted by high pressure homogenization. The cell-debris is separated from the oleate hydratase containing liquid phase and discarded.

The resulting lysate is then used for the hydration of the FFAs-fraction from step 1). The reaction is carried out in an aqueous system at low temperatures under constant mixing. After an appropriate reaction time the product (10-HSA) can be separated from the reaction mixture by one of the methods described above.

5.) Scale-Up of the 10-HSA Production from Oleic Acid by the Oleate Hydrates from *Stenotrophomonas maltophilia*

5.1.) Pre-tests for the conversion of oleic acid (OA) to 10-hydroxystearic acid (10-HSA) by the oleate hydrates (OH) from *Stenotrophomonas maltophilia* (ohySm):

TABLE 1

Conversion of oleic acid (OA) to 10-hydroxystearic acid (10-HSA) by the oleate hydrates (OH) from *Stenotrophomonas maltophilia* (ohySm) under different reaction conditions (variation of culture conditions and reaction time)

| Sample | Reaction type | Specification | reaction time [h] |
|---|---|---|---|
| 1 | flat flask (300 ml) | $1^{st}$ run | 2 |
| 1.1 | | $2^{nd}$ run (recycle) | 1.5 |
| 2 | baffled flask (300 ml) | $1^{st}$ run | 1.5 |
| 2.1 | | $2^{nd}$ run (recycle) | 1.5 |
| 3 | stirrer 500 rpm | $1^{st}$ run | 1.5 |
| 3.1 | | $2^{nd}$ run (recycle) | 1.5 |
| 4 | stirrer 750 rpm | $1^{st}$ run | 2.5 |
| 5 | | $1^{st}$ run | 1.5 |

In order to check the activity of the different samples, said samples are extracted and fractions of each sample are spotted on TLC plates (see FIG. 5).

The results of the activity tests, in different reaction vessels and by different mixing methods, showed a high conversion level of OA to 10-HSA by oleate hydratase from ohySm (FIG. 5). No loss in activity is detected after the recycling of the enzyme solution.

5.2.) New pre-tests for filtering the final reaction mixture with miracloth (rayon-polyester+acrylic binder) filtering fabric. Beaker+magnetic stirrer at 250 rpm standard conditions in duplicate. Filtering after first 90 min worked very well.

The resulting pellet size of the two preparation were documented (FIG. 6) The following samples were collected:

TABLE 2

Overview of sample set for the filtration test

| sample name | description |
|---|---|
| 1 | sample after $1^{st}$ reaction A |
| 2 | sample after $1^{st}$ reaction B |
| 3 | sample after $1^{st}$ filtration A |
| 4 | sample after $1^{st}$ filtration B |
| 5 | sample after $2^{nd}$ reaction A |
| 6 | sample after $2^{nd}$ filtration A |
| 7 | sample after $2^{nd}$ filtration B |
| 8 | sample after $3^{rd}$ reaction A |
| M | page-ruler unstained marker |
| OA | oleic acid |
| 10-HSA | 10-hydroxystearic acid |

TABLE 3

Results of recovery rate of conversion of oleic acid (OA) to 10-hydroxystearic acid (10-HSA) with oleate hydratase from *S. maltophilia* after a first and second reaction (50 mM Phosphate- Citrate-Buffer, pH 6.5, at 35° C.). Preparation 1 and 2 have been tested independently under the same conditions.

| | reaction 1 | | reaction 2 (recycle) | |
|---|---|---|---|---|
| | enzyme solution recovery [%] | Filter cake [g] | Enzyme solution recovery [%] | Filter cake [g] |
| preparation 1 | 80 | 6.3 | 90 | 0.38 |
| preparation 2 | 86 | 6.8 | 93 | 0.66 |

After the $2^{nd}$ reaction almost no product is filtered out by the miracloth anymore, suggesting that the enzyme got inactivated (either during the process or by the filtering with the miracloth) or got adsorbed by the filtering material.

To eliminate the possibility of a binding of the enzyme to the filtering material, an SDS-PAGE with samples collected from all fractions was prepared (FIG. 7).

The SDS-PAGE showed no loss of protein in all fractions. These results eliminate the option of potential interactions between the protein and the filtering cloth.

The activity tests of the different samples by extraction and TLC monitored on TLC plates (FIG. 8) show a high conversion rate of OA to 10-HSA by the oleate hydratase from *Stenotrophomonas maltophilia* and an excellent filtering performance for the cloth. The TLC plates also show a high conversion rate after the $1^{st}$ recycling step. Although the 10-HSA couldn't be found as big aggregates (unlike after the $1^{st}$ reaction), it got adsorbed by the filtering material, because the product couldn't be identified in the fraction after the filtration step. Lane 8 shows the extraction result after the $2^{nd}$ recycling of the enzyme. As it was unclear whether the reaction from the previous step worked correctly (see results of table 3 above), no new substrate was added to the reaction mixture, explaining the low amounts of substrate and product in this lane.

In the next step the filter cake and the filtering cloth was directly extracted with EtOAc and the fractions are spotted on TLC plates (FIG. 9).

The extraction results of the filter cake and the filtering cloth are shown in FIG. 5. Lane 1 is the first extraction of the filter cake (in duplicate) with 45 ml of EtOAc. As the filter cake could not be dissolved in 45 ml of EtOAc, the remaining solids were spun down, the EtOAc phase was decanted to a fresh tube and an additional 45 ml of EtOAc were added to the sample. In this step almost all solid flakes were dissolved and the EtOAc fraction was spotted on the TLC plate (2; in duplicate). Lane C1 depicts the results obtained from the direct extraction of approx. 17.5 cm² of filtering cloth with 35 ml of EtOAc. As not all of the bound 10-HSA flakes could be dissolved from the tissue, the EtOAc phase was again decanted to a fresh tube and an additional 25 ml of EtOAc were added to the sample. The result of this $2^{nd}$ extraction is shown in lane C2. Lane CC is the negative control resulting from the extraction of an unused piece of cloth and is not showing any detectable spots on the TLC plate, suggesting that the cloth is stable towards EtOAc as an organic solvent.

6.) Scaled Reaction from 50 L Fermentation of the 10-HSA Production from Oleic Acid by the Oleate Hydrates from *Stenotrophomonas maltophilia*

TABLE 4

Concentration of culture medium ingredients in g/l Riesenberg MM

| | | Conc. g/l | handling |
|---|---|---|---|
| C-source | glucose | 2 | autoclave separately |
| salts | KH2PO4 | 13.3 | autoclave |
| | (NH4)2PO4 | 4 | |
| | NaOH | 2.4 | |
| | citric acid | 1.7 | |
| | MgSO4*7H2O | 1.2 | autoclave separately |
| trace elements | EDTA | 0.0084 | sterile filtration |
| | CoC2*6H2O | 0.0025 | |
| | MnCl2*4H2O | 0.015 | |
| | CuCl2*2H2O | 0.0015 | |
| | H3BO4 | 0.003 | |
| | Na2MoO4*2H2O | 0.0025 | |

TABLE 4-continued

Concentration of culture medium ingredients in g/l Riesenberg MM

| | | Conc. g/l | handling |
|---|---|---|---|
| | Zn(CH3COO)2*2H2O | 0.013 | |
| | Fe(III)citrat | 0.1 | |
| feed | glucose | 300 | |

TABLE 5

Composition of culture medium (share in the total volume)

50 L reactor volume

| | |
|---|---|
| -2 L | safety volume |
| -5 L | feed glucose |
| -1 L | MgSO4 solution |
| -0.86 L | trace elements |
| -0.5 L | batch glucose |
| -0.05 L | Kanamycin |
| 40.59 L | including the remaining medium ingredients |

The automatic recording of the fermentation parameter are shown in FIG. 10

7.) Conversion Reaction

After the separation of the cells with the disc type separator 3 batches of concentrated cells (each approx. 1.5 kg, samples 1-3) were stored at −20° C.

After defrosting the concentrated cells at 4° C. for 3 days samples were taken from every single batch for protein determination and the batches were combined and filled up with phosphate-citrate buffer to a final volume of 8 l. After mixing the concentrated cells homogeneously with the buffer, the cells were subsequently disrupted by high pressure homogenization (HPH). After 4 passages of homogenization (sample 4) the disrupted cells were filtered in two stages, using a (unqualified) 0.5 µm (sample 5) and a 0.2 µm (sample 6) filter cartridge.

For a further separation of the cell debris (to prevent a later extraction of cell-wall lipids), a purification of the protein via cross-flow (x-flow) filtration was carried out. The x-flow was equipped with a 300 kDa PES filter cassette and the disrupted cells were filtered until the retentate reached a volume of 4 L, the permeate (samples 7+9) was collected in a 20 L canister. Subsequently dialysis was started with 13 L of phosphate-citrate buffer and ran over night. The retentate (sample 8) was kept at 4° C. and the permeate was concentrated with a 30 kDa PES filter cassette to a final volume of 1 L.

Samples (Table 6) for protein and activity determination were taken from every stage of the process and analyzed by SDS-PAGE (FIGS. 11 and 12) or TLC. The samples for the SDS-PAGE were diluted 1:3 with 8 M urea to prevent an overload of the gel.

TABLE 6

Protein samples taken during process

| sample name | description |
|---|---|
| 1 | concentrated cells $1^{st}$ batch |
| 2 | concentrated cells $2^{nd}$ batch |
| 3 | concentrated cells $3^{rd}$ batch |

TABLE 6-continued

Protein samples taken during process

| sample name | description |
|---|---|
| 4 | after HPH |
| 5 | after 0.5 μm filter |
| 6 | after 0.2 μm filter |
| 7 | permeate start 300 kDa filtration |
| 8 | retentate after 300 kDa filtration |
| 9 | permeate end of 300 kDa filtration |

The SDS-PAGE showed only small bands for the overexpression of the oleate hydratase (69 kDa) in all three batches (1-3). No difference could be detected after the HPH procedure, the filtering with 0.2 and 0.5 μm filters shows a slight decrease of unwanted proteins, respectively. Lanes 7-9 showed that all proteins, including the expressed oleate hydratase, were refrained by the filtering cassette, suggesting that an unexpected problem with the filtering cassettes existed.

As the retentate was of a dark brownish color and still containing high amounts of particulate matter a test extraction with ethyl acetate was done (FIG. 13), to ensure that no remaining lipids from the bacterial cell wall will affect the following production and extraction steps.

The TLC plate didn't show any bands that would indicate lipids in the extracted samples. To determine the enzymatic activity of the different fractions obtained during the process and to ensure an adequate conversion rate (due to low protein expression levels), 1 ml activity tests were carried out with the samples 4-9 (FIG. 14).

The TLC plate after the activity tests showed high conversion rates for the samples 4-6 as well as for sample 8 (in duplicate). The conversion rates for the samples 7 & 9 were (as expected from the SDS-PAGE) very low.

Based on the results from the SDS-PAGE and activity tests the conversion of the oleic acid was carried out with the retentate (sample 8) and the concentrated permeate (after 30 kDa filtration, sample not shown).

The 5 L of protein solution (4 L retentate+1 concentrated permeate) were distributed equally into two 5 L flasks, placed on a magnetic stirring plate (400 rpm) inside an incubator and heated to the reaction temperature of 35° C. During the warming process, 2.82 L of phosphate-citrate buffer were mixed with 180 ml (z 160 g=2% w/v) of oleic acid and mixed on a magnetic stirring plate. After the protein solutions reached 35° C. they were filled up to 4 L volume with the mixture of buffer and substrate and incubated for 90 min under constant stirring. A sample was taken from the reaction mixture after 60 min to monitor the enzymatic activity (FIG. 15). The formation of clearly visible white flakes of 10-HSA was observed during the reaction.

The results from the TLC plate (FIG. 15) showed very high conversion rates from oleic acid to 10-hydroxystearic acid.

After 90 min of reaction time, the product was separated from the reaction mixture by a filtration step with miracloth fabric (4 layers). The filtering step resulted in a semi-solid filter cake and showed a good performance in the product separation.

TABLE 7

Filtration results after using miracloth fabric cloth.
The filter cake has been weighed and the loss of
liquid using filtration has been documented.

| Preparation | Filter cake [g] | Loss of vol. [ml] |
|---|---|---|
| 1 | 296.3 | 500 |
| 2 | 222.9 | 500 |

After the filtration the remaining enzyme solution was refilled to a volume of 4 L with a mixture of buffer and substrate to a final substrate concentration of 2% (w/v) and incubated for 90 min at 35° C. During the reaction time the reaction mixture appeared as a high viscose, jellylike liquid with only very small 10-HSA flakes visible. After the reaction time the mixture was exposed to the miracloth fabric for the second filtration (FIG. 16).

8.) Separation of the 10-HSA Product from the Recycled Enzyme Solution

Probes of the reaction mixture were filled in centrifuge beakers and centrifuged for 30 min at 4° C. and 12200 g. After the centrifugation a semi-solid pellet appeared which showed three different layers. The supernatant remained cloudy after the centrifugation step. The resulting pellets had a weight of approx. 250 g, a 12.5 times higher weight then the inserted substrate of 20 g/L. Although the pellets still include high amounts of water and protein the centrifugation was the most successful approach for the separation of product and enzyme solution and could reduce the volume to be extracted by 75%. The pellets were subsequently dried at 50° C. to further reduce the water content (see FIG. 17).

200 ml of the resulting supernatant were taken for a $2^{nd}$ recycling test of the enzyme solution. 2% (w/v) of fresh substrate were added to the solution and the sample was incubated over night at 35° C. under constant stirring (250 rpm). The texture of the reaction solution did not differ from the texture of the $1^{st}$ recycling step (jellylike, highly viscose liquid), suggesting that the enzyme was still active. For the separation of the product from the reaction solution a sixth approach was tested. 1.5 g (=1% w/v) of hydrophobic Amberlite XAD2 beads were added to 150 ml of the reaction mixture and stirred for 1 h. It was thereby tested, whether the hydrophobic beads could trigger the aggregation of the 10-HSA inside the solution by acting as a nucleus for bigger aggregates. After the reaction time no bigger flakes of 10-HSA were visible and the filtering properties of the solution via miracloth fabric were as problematic as described above.

Samples were taken from the separation approach to monitor the enzymatic activity and the separation efficiency (FIG. 18).

Results shown in FIG. 18

TABLE 8

Sample description and respective results

| sample name | description | results |
|---|---|---|
| *1st enzymatic reaction* | | |
| 12 (0.1 g) | filter cake 1, after 1st reaction | High conversion rate, high amount of product |
| *2nd enzymatic reaction (1st recycling step)* | | |
| 13 (0.35 g) | remaining mixture from cloth on funnel over night | High conversion rate, high amount of product |
| 14 (0.35 g) | corresponding filtrate of sample 13 | Almost all FAs filtered from mixture |
| 15 (0.35 g) | supernatant after centrifugation | Almost all FAs filtered from mixture (slight increase towards sample 14) |
| 16a (0.35 g) | outer layer of the centrifugation pellet | The deeper the layer, the more product (and substrate) is seen. Correlation between product and substrate is similar and clearly on the product side |
| 16b (0.35 g) | middle layer of the centrifugation pellet | |
| 16c (0.35 g) | inner layer of the centrifugation pellet | |
| 17 (0.35 g) | upper phase of samples rested at 4° C. over night | Lower amounts of product and substrate, compared to downer phase → air inside the mixture |
| 18 (0.35 g) | downer phase of samples rested at 4° C. over night | High amounts of product and substrate |
| *3rd enzymatic reaction (2nd recycling step)* | | |
| 19 (0.35 g) | sample from 2nd recycling over night at 35° C. | 2nd recycling step showed same results like the two reactions before, very god conversion rate |

Description of Conditions During Process for the Production of 10-HSA

TABLE 9

Overview of reaction conditions

| Instrument/System | Description |
|---|---|
| Cross Flow | Flowrate (0-100%) 0-1250 L h$^{-1}$, used range: 12-15%; Inlet-pressure 2.0-2.7 bar. Retentat- and Permeat-pressure 0 bar, Performed at 4° C. |
| Filtration Cassette | Concentration of Pre-Filtrate from 8 L to 4 L and Diafiltration with 12 L Buffer |
| Filtration Cassette | Concentration of the Diafiltrate from 12 L to 1 L |
| Pre-Filtration | Filterholder with ½" TC-Clamp connection and for 5" Cartridges (0.5 m$^2$), Performed at Room temperature |
| Filter Step 1 | Filtration of the 8 L Cell lysate: Pressure drop of 0.2-0.5 bar at the end, at a Flow rate of 250 mL min$^{-1}$ |
| Filter Step 2 | Filtration of the 8 L Cell lysate: Pressure Drop of 0.3-1.2 bar at the end, at a Flow rate of 200 mL min$^{-1}$ |
| Pump and Setup | Speed (0-100%) 0-120 rpm. Tube with ¼" inner diameter, Filtration performed at 40-60% |
| Cell Disruption | Flowrate of 100 L h$^{-1}$ at a Pressure of 900 bar (single-stage Homogenizing valve); 4 recirculation (repeats of passing through homogenizer) in a 10 L stirred flask (8 L of Cell lysate) in an ice bath, Temperature kept under 40° C. |
| Cell harvest | Harvesting with a Flow rate of 80-100 L h–1. Discontinuous cell ejection every 20 L. At least 5 L harvested. Final optical Density (at 600 nm) of about 250 |
| Fermentation | Parameter of Cultivation see Chapter Fermentation 50 L |
| Mixing | Magnetic stirrers for 1-3 L and 5-10 L Flask; Used stirring speeds from 150-450 rpm |

Summary

Two conversion reactions were carried out (in parallel) in a 4 L scale for 90 min at 35° C. with 2% (w/w) of Substrate (OA) under constant stirring. The produced 10-HSA could be successfully filtered from the reaction mixture and the remaining enzyme solution was used for a second (recycling) conversion reaction, without a detectable loss of enzymatic activity. It was furthermore shown that a third reaction (2$^{nd}$ recycling reaction) can be carried out without detectable reduction of the enzymatic activity. In total, 320 g of oleic acid have been converted within 4 separate reactions.

Product Separation:

The yield of the filtering performance using miracloth fabric was very high. TLC plate analyses show that almost all product (10-HSA) has been separated by filtration. The proportions which have passed the filter are in the lower single-digit percent area.

Scheme 5 as shown in FIG. 20: Scheme for a technical setup in order to scale up the process of the present application The claimed process of the present application for the production of 10-HSA can be performed in a technical set-up comprising a bioreactor, a disc-type separator, a high-pressure homogenizer, a device for cross-flow filtration and enzymatic conversion.

Summary of Some Embodiments

1. Process for the cell-free enzymatic production of 10-hydroxystearic acid (10-HSA) comprising the following steps:
   1) Enzymatic hydrolysis of oil comprising at least 25% oleic acid using lipase to provide free fatty acids comprising oleic acid, and
   2) Hydration of the free fatty acids using oleate-hydratase (EC 4.2.1.53), wherein the oleate-hydratase is selected from *Stenotrophomonas maltophilia* or derivatives thereof having at least 10% activity when compared with wild-type enzyme under the same conditions or active fragments thereof and/or *Rhodococcus erythropolis* or derivatives thereof having at least 10% activity when compared with wild-type enzyme under the same conditions or active fragments thereof, and
   3) Separation of 10-HSA in form of a filter cake from the reaction mixture, and
   4) Purification of 10-HSA from the separated filter cake, and wherein, optionally, the lipase and/or the hydratase used in step 1) and/or step 2) is/are recycled and/or immobilised.
2. The process according to embodiment 1, wherein said oil is selected from the group comprising renewable/regrowing feedstocks.
3. The process according to embodiment 1 or 2, wherein said feedstocks are selected from the group comprising animals, plants and microorganisms.
4. The process according to any of the preceding embodiments, wherein said oil comprises triglycerids with an oleic acid content ≥40%, preferably ≥50%, more preferably ≥70%.
5. The process according to any of the preceding embodiments, wherein said oil is a plant oil selected from the group comprising vegetable oil, castor oil, tree borne oil, olive oil, mustard oil, linseed oil, canola oil, coconut oil, coriander oil, corn oil, cottonseed oil, hazelnut oil, neem oil, palm oil, peanut oil, rapeseed oil, rice bran oil, safflower oil, soybean oil, sunflower seed oil, and mixtures thereof.
6. The process according to any of the preceding embodiments, wherein said oil is an animal oil selected from the group comprising tall, fish and crustacean oil.
7. The process according to any of the preceding embodiments, wherein said oil is a microbial oil.
8. The process according to embodiment 7, wherein said microbial oil is derived from bacteria, yeast, algae and/or fungi.
9. The process according to any of the preceding embodiments, wherein the enzymatic hydrolysis of oil using lipase (step 1) and the hydration using oleate hydratase (step 2) can be carried out sequentially or simultaneously.
10. The process according to any of the preceding embodiments, wherein said lipase is selected from the group comprising mono-, di- or triglyceride lipase.
11. The process according to any of the preceding embodiments, wherein said lipase is a lipase selected from the EC class of hydrolases (EC class 3.), preferably from the EC class of esterase enyzmes acting on ester bonds (EC class 3.1), more preferably from the class of carboxylic-ester hydrolases (EC class 3.1.1).
12. The process according to any of the preceding embodiments, wherein said lipase is a lipase selected from the EC class EC 3.1.1.3.
13. The process according to any of the preceding embodiments, wherein said triglyceride lipase is lipase selected from the group comprising *Candida rugosa* lipase, lipase from porcine pancreas, lipase from *Rhizopus oryzae* or lipase from *Pseudomonas* sp.
14. The process according to any of the preceding embodiments, wherein said enzymatic hydrolysis is carried out in an aqueous system.
15. The process according to any of the preceding embodiments, wherein said aqueous system comprises at least one buffer and/or at least one solvent, mixtures of solvents and/or mixtures of buffer(s) and solvent(s).
16. The process according to any of the preceding embodiments, wherein said buffer is selected from Tris-HCl buffer, phosphate-citrate-buffer, 3-(N-morpholino)propanesulfonic acid (MOPS) buffer.
17. The process according to any of the preceding embodiments, wherein the concentration/amount of said buffer is in the range of 10 mM to 100 mM.
18. The process according to any of the preceding embodiments, wherein said enzymatic hydrolysis is carried out at a temperature ranging from 10° C. to 60° C.
19. The process according to any of the preceding embodiments, wherein said enzymatic hydrolysis is carried out for a period of 15 to 300 minutes, preferably 30 to 180 minutes, more preferably 60-90 min
20. The process according to any of the preceding embodiments, wherein after the enzymatic hydrolysis (step 1) said free fatty acids are optionally separated from the reaction mixture by at least one washing/purification step.
21. The process according to any of the preceding embodiments, wherein after the enzymatic hydrolysis (step 1), said free fatty acids are separated from glycerol in at least one washing/purification step by extraction or phase separation.
22. The process according to any of the preceding embodiments, wherein after the 50 enzymatic hydrolysis (step 1) said free fatty acids are optionally separated from the reaction mixture by at least one washing/purification step using at least one organic solvent and/or an aqueous system.
23. The process according to embodiment 22, wherein said organic solvent is selected from the group ethylacetate, hexane, toluene, methyl isobutyl ketone (MIBK), methanol, ether.
24. The process according to any of the preceding embodiments, wherein said hydration using oleate-hydratase (step 2) is carried out in an aqueous system.
25. The process according to any of the preceding embodiments, wherein said aqueous system for the hydration comprises buffer, free fatty acids as substrate, oleate hydratase and/or emulsifier.
26. The process according to any of the preceding embodiments, wherein said buffer is selected from Tris-HCl buffer, phosphate-citrate-buffer, 3-(N-morpholino)propanesulfonic acid (MOPS) buffer, 2-(N-morpholino)ethanesulfonic acid (MES) buffer, piperazine-N,N'-bis(2-ethanesulfonic acid) (PIPES); 4-(2-hydroxyethyl)-1-piperazineethanesulfonic acid (HEPES); Sorensen's phosphate buffer (Stock solutions: A 0.2 M $NaH_2PO_4$, B 0.2 M $Na_2HPO_4$).
27. The process according to any of the preceding embodiments, wherein said hydration is carried out at a temperature ranging from 10° C. to 50° C., preferably 20-40° C., more preferably 25-35%.
28. The process according to any of the preceding embodiments, wherein said hydration is carried out for a period of 10 to 300 minutes, preferably 30 to 180 minutes, more preferably 60 to 90 minutes.

29. The process according to any of the preceding embodiments, wherein the hydration is carried out under constant mixing, wherein the speed is in the range of 250 to 750 rpm.
30. The process according to any of the preceding embodiments, wherein after the hydration (step 2) 10-HSA is separated from the reaction mixture in form of a filter cake using filtration and/or centrifugation and/or using chromatographic methods.
31. The process according to any of the preceding embodiments, wherein after the hydration (step 2), 10-HSA is prepared from the filter cake using extraction with at least one organic solvent and/or using phase generation.
32. The process according to any of the preceding embodiments, wherein after the hydration (step 2), 10-HSA is prepared from the filter cake using extraction with at least one organic solvent, wherein said organic solvent is selected from the group comprising ethyl acetate, hexane, methanol, ether, methyl-isobutyl-ketone, toluene.
33. The process according to embodiments 31-32, wherein the concentration of said organic solvent is between 80% w/v to 100% w/v.
34. The process according to embodiments 31-33, wherein the concentration of said 50 organic solvent is ≤90% w/v.
35. The process according to any of the preceding embodiments, wherein after the extraction of 10-HSA from the filter cake, purification of 10-HSA is performed (step 4) using phase separation.
36. The process according to any of the preceding embodiments, wherein said purification of 10-HSA from the filter cake (step 4) is performed by phase separation, wherein the dissolved 10-HSA is separated from the residual fraction/reaction mixture comprising water and enzymes in form of a filter cake using filtration and/or centrifugation and/or using chromatographic methods, and wherein, optionally, 10 HSA flocks are separated from the mixture by filtration or gravimetric solid-liquid-separation.
37. The process according to any of the preceding embodiments, wherein said purification of 10-HSA from the filter cake (step 4) is performed by phase separation, wherein 10-HSA is dissolved in at least one organic solvent.
38. The process according to embodiment 37, wherein said organic solvent is selected from the group comprising ethyl acetate, hexane, methanol, ether, methyl-isobutyl-ketone, toluene.
39. The process according to embodiments 37-38, wherein the concentration of said organic solvent is between 80% w/v to 100% w/v.
40. The process according to embodiments 37-39, wherein the concentration of said organic solvent is ≤90% w/v.
41. The process according to embodiments 37 to 40, wherein the organic solvent is removed by evaporation, distilling, gassing with nitrogen and/or phase separation.
42. Composition or product comprising 10-HSA obtainable by the process according to any of the preceding embodiments, wherein, preferably, said composition or product is selected from specialty oleochemicals, chemical performance additives, cosmetics, cosmetic additives, in particular lubricants.

The invention claimed is:

1. A process for cell-free enzymatic production of 10-hydroxystearic acid (10-HSA) comprising the following steps:
   1) enzymatic hydrolysis of oil comprising at least 25% oleic acid using lipase to provide free fatty acids comprising oleic acid, and
   2) hydration of the free fatty acids, to create a reaction mixture, using oleate-hydratase (EC 4.2.1.53), wherein the oleate-hydratase is selected from *Stenotrophomonas maltophilia* or derivatives thereof having at least 10% activity when compared with wild-type enzyme under the same conditions or active fragments thereof and/or *Rhodococcus erythropolis* or derivatives thereof having at least 10% activity when compared with wild-type enzyme under the same conditions or active fragments thereof, and
   3) separation of 10-HSA in form of a filter cake from the reaction mixture, and
   4) purification of 10-HSA from the separated filter cake, wherein the purification comprises extracting 10-HSA with at least one organic solvent and separating 10-HSA dissolved in the at least one organic solvent using by phase separation from a residual fraction comprising water and enzymes, and wherein, optionally, the lipase and/or the hydratase used in step 1) and/or step 2) is/are recycled and/or immobilised.

2. The process according to claim 1, wherein said oil is selected from renewable/regrowing feedstocks.

3. The process according to claim 2, wherein said feedstocks are derived from animals, plants and microorganisms.

4. The process according to claim 1, wherein said oil comprises triglycerides with an oleic acid content ≥40%.

5. The process according to claim 1, wherein said oil is a plant oil selected from vegetable oil, castor oil, tree borne oil, olive oil, mustard oil, linseed oil, canola oil, coconut oil, coriander oil, corn oil, cottonseed oil, hazelnut oil, olive oil, neem oil, palm oil, peanut oil, rapeseed oil, rice bran oil, safflower oil, soybean oil, sunflower seed oil, and mixtures thereof.

6. The process according to claim 1, wherein said oil is an animal oil selected from tall, fish and crustacean oil.

7. The process according to claim 1, wherein said oil is a microbial oil.

8. The process according to claim 7, wherein said microbial oil is derived from bacteria, yeast, algae and/or fungi.

9. The process according to claim 1, wherein the enzymatic hydrolysis of oil using lipase (step 1) and the hydration using oleate hydratase (step 2) are carried out simultaneously.

10. The process according to claim 1, wherein said lipase is mono-, di- or triglyceride lipase.

11. The process according to claim 1, wherein said lipase is a lipase selected from the EC class of esterase enzymes acting on ester bonds (EC class 3.1).

12. The process according to claim 1, wherein said triglyceride lipase is *Candida rugosa* lipase, or lipase from porcine pancreas, lipase from *Rhizopus oryzae* or lipase from *Pseudomonas* sp.

13. The process according to claim 1, wherein said enzymatic hydrolysis is carried out in an aqueous system.

14. The process according to claim 1, wherein after the enzymatic hydrolysis (step 1) said free fatty acids are separated by at least one washing/purification step.

15. The process according to claim 1, wherein after the hydration (step 2) 10-HSA is separated from the reaction mixture in form of a filter cake using filtration and/or centrifugation and/or using chromatographic methods, and wherein, 10 HSA flocks are separated from the mixture by filtration or gravimetric solid-liquid-separation.

16. The process according to claim 1, further comprising preparing a composition comprising said 10-HSA, wherein said composition is selected from chemical performance additives, cosmetics, and cosmetic additives.

17. The process according to claim 4, wherein the oleic acid content is ≥70%.

18. The process according to claim 11, wherein the lipase is selected from the class of carboxylic-ester hydrolases (EC class 3.1.1).

19. The process according to claim 16, wherein the composition is a lubricant.

* * * * *

SEQUENCE LISTING

```
<160> NUMBER OF SEQ ID NOS: 12

<210> SEQ ID NO 1
<211> LENGTH: 559
<212> TYPE: PRT
<213> ORGANISM: Rhodococcus erythropolis
<220> FEATURE:
<221> NAME/KEY: MISC_FEATURE
<222> LOCATION: (1)..(559)
<223> OTHER INFORMATION: Abbreviated in Fig. 1 as Rre or Rer

<400> SEQUENCE: 1

Met Ser Ser Asn Leu Ser His Lys Ala Tyr Met Ile Gly Ala Gly Ile
1               5                   10                  15

Gly Asn Leu Ser Ala Ala Val Tyr Leu Ile Arg Asp Gly Glu Trp Asn
            20                  25                  30

Gly Glu Asp Ile Thr Ile Met Gly Leu Asp Met His Gly Ala Asn Asp
        35                  40                  45

Gly Glu Ser Ala Ala Thr Phe Gln His Gln Tyr Gly His Arg Glu Leu
    50                  55                  60

Gly Asn Asp Ala Gly Phe Ile Asn Arg Gly Gly Arg Met Leu Asn Glu
65                  70                  75                  80

Glu Thr Tyr Glu Asn Leu Trp Asp Val Leu Ser Ala Val Pro Ser Leu
                85                  90                  95

Asp Asn Pro Gly Lys Ser Val Thr Asp Asp Ile Leu Asp Phe Asp His
            100                 105                 110

Ala His Pro Thr His Asp Val Ala Arg Leu Ile Asp Arg Asp Gly Ile
        115                 120                 125

Arg Asn Lys Gly Glu Asn Asp Tyr Lys His Met Gln Phe Asp Asn Lys
    130                 135                 140
```

```
Asp Arg Tyr Leu Leu Thr Lys Leu Met Thr Met Pro Glu Ser Asp Glu
145                 150                 155                 160

Ala Lys Leu Asp Asp Ile Ser Ile Glu Gln Trp Phe Glu Glu Thr Pro
            165                 170                 175

His Phe Phe Thr Thr Asn Phe Trp Tyr Met Trp Glu Thr Thr Phe Ala
                180                 185                 190

Phe Lys Arg Val Ser Ser Ala Met Glu Leu Arg Arg Tyr Met Asn Arg
        195                 200                 205

Met Ile Leu Glu Phe Ser Arg Ile Gln Thr Leu Ala Gly Val Thr Arg
    210                 215                 220

Ser Pro Tyr Asn Gln Tyr Glu Ser Ile Ile Leu Pro Met Arg Thr Phe
225                 230                 235                 240

Leu Glu Gly Lys Gly Val Lys Phe Val Asn Glu Leu Lys Ile Thr Glu
                245                 250                 255

Phe Val Phe Lys Asp Thr Pro Leu Arg Asp Glu Ile Ile Val Thr Gly
            260                 265                 270

Leu Asp Tyr Glu Asn Val Arg Thr Gly Glu Lys Gly Arg Ile Asp Val
        275                 280                 285

Ala Glu Gly Asp Phe Val Phe Asp Thr Asn Gly Ser Ile Thr Asp Ser
290                 295                 300

Ser Ser Ile Gly Asp Leu Asp Thr Pro Ile Val Glu Asp Met Arg Tyr
305                 310                 315                 320

Ala Pro Ser Ala Leu Leu Trp Lys Gln Ala Thr Glu His Phe Tyr Asp
                325                 330                 335

Leu Gly Asn Pro Asp Lys Phe Phe Gly Asp Arg Ala Gln Ser Glu Trp
            340                 345                 350

Thr Ser Phe Thr Val Thr Thr Ser His Glu Leu Ile Asn Glu Ile
        355                 360                 365

Ser Arg Ile Thr Lys Gln Leu Pro Gly Asn Ala Leu Asn Thr Phe Val
    370                 375                 380

Asp Ser Asn Val Leu Leu Ser Ile Val Val His His Gln Pro His Tyr
385                 390                 395                 400

His Ala Gln Lys Glu Asn Glu Gly Val Phe Trp Gly Tyr Cys Leu Phe
                405                 410                 415

Pro Arg Lys Asp Gly Asp Tyr Val Lys Lys Pro Phe Ile Glu Met Thr
            420                 425                 430

Gly Arg Glu Met Leu Glu Glu Thr Leu Gly His Leu Glu Ala Leu Asp
        435                 440                 445

Glu Ser Gly Thr Leu Ala Ala Arg Arg Gln Glu Ile Met Asp Ser Val
450                 455                 460

Val Asn Ser Ile Pro Ser His Met Pro Tyr Ala Ser Ala Leu Phe Asn
465                 470                 475                 480

Arg Arg Ala Val Gly Asp Arg Pro Leu Val Val Pro Lys His Ser Lys
                485                 490                 495

Asn Leu Ala Phe Ile Ser Gln Phe Ala Glu Leu Pro Phe Asp Met Val
            500                 505                 510

Phe Thr Glu Gln Tyr Ser Val Arg Cys Ala Gln Val Ala Val Tyr Lys
        515                 520                 525

Phe Leu Gly Ile Pro Glu Asp Lys Leu Thr Lys Met His His Tyr Glu
        530                 535                 540

Lys Asp Pro Lys Val Leu Ala Lys Ala Val Thr Met Phe Arg
545                 550                 555
```

```
<210> SEQ ID NO 2
<211> LENGTH: 589
<212> TYPE: PRT
<213> ORGANISM: Stenotrophomonas maltophilia
<220> FEATURE:
<221> NAME/KEY: MISC_FEATURE
<222> LOCATION: (1)..(589)
<223> OTHER INFORMATION: Abbreviated in Fig. 1 as Sma

<400> SEQUENCE: 2
```

Met Tyr Tyr Ser Ser Gly Asn Tyr Glu Ala Phe Ala Arg Pro Arg Lys
1               5                   10                  15

Pro Ala Gly Val Asp Gly Lys Arg Ala Trp Phe Val Gly Ser Gly Leu
            20                  25                  30

Ala Ser Leu Ala Gly Ala Ala Phe Leu Ile Arg Asp Gly Arg Met Ala
        35                  40                  45

Gly Glu Arg Ile Thr Ile Leu Glu Gln Gln His Ile Pro Gly Gly Ala
50                  55                  60

Leu Asp Gly Leu Lys Val Pro Glu Lys Gly Phe Val Ile Arg Gly Gly
65                  70                  75                  80

Arg Glu Met Glu Asp His Phe Glu Cys Leu Trp Asp Leu Phe Arg Ser
                85                  90                  95

Ile Pro Ser Leu Glu Ile Glu Asp Ala Ser Val Leu Asp Glu Phe Tyr
            100                 105                 110

Trp Leu Asn Lys Asp Asp Pro Asn Tyr Ser Leu Gln Arg Ala Thr Ile
        115                 120                 125

Asn Arg Gly Glu Asp Ala His Thr Asp Gly Leu Phe Thr Leu Thr Glu
130                 135                 140

Gln Ala Gln Lys Asp Ile Ile Ala Leu Phe Leu Ala Thr Arg Gln Glu
145                 150                 155                 160

Met Glu Asn Lys Arg Ile Asn Glu Val Leu Gly Arg Asp Phe Leu Asp
                165                 170                 175

Ser Asn Phe Trp Leu Tyr Trp Arg Thr Met Phe Ala Phe Glu Glu Trp
            180                 185                 190

His Ser Ala Leu Glu Met Lys Leu Tyr Leu His Arg Phe Ile His His
        195                 200                 205

Ile Gly Gly Leu Pro Asp Phe Ser Ala Leu Lys Phe Thr Lys Tyr Asn
210                 215                 220

Gln Tyr Glu Ser Leu Val Leu Pro Leu Val Lys Trp Leu Gln Asp Gln
225                 230                 235                 240

Gly Val Val Phe Gln Tyr Gly Thr Glu Val Thr Asp Val Asp Phe Asp
                245                 250                 255

Leu Gln Pro Asp Arg Lys Gln Ala Thr Arg Ile His Trp Met His Asp
            260                 265                 270

Gly Val Ala Gly Val Asp Leu Gly Ala Asp Leu Leu Phe Met
        275                 280                 285

Thr Ile Gly Ser Leu Thr Glu Asn Ser Asp Asn Gly Asp His His Thr
290                 295                 300

Ala Ala Arg Leu Asn Glu Gly Pro Ala Pro Ala Trp Asp Leu Trp Arg
305                 310                 315                 320

Arg Ile Ala Ala Lys Asp Asp Ala Phe Gly Arg Pro Asp Val Phe Gly
                325                 330                 335

Ala His Ile Pro Glu Thr Lys Trp Glu Ser Ala Thr Val Thr Thr Leu
            340                 345                 350

Asp Ala Arg Ile Pro Ala Tyr Ile Gln Lys Ile Ala Lys Arg Asp Pro
        355                 360                 365

-continued

```
Phe Ser Gly Lys Val Val Thr Gly Gly Ile Val Ser Val Arg Asp Ser
    370                 375                 380

Arg Trp Leu Met Ser Trp Thr Val Asn Arg Gln Pro His Phe Lys Asn
385                 390                 395                 400

Gln Pro Lys Asp Gln Ile Val Val Trp Val Tyr Ser Leu Phe Val Asp
                405                 410                 415

Thr Pro Gly Asp Tyr Val Lys Lys Pro Met Gln Asp Cys Thr Gly Glu
            420                 425                 430

Glu Ile Thr Arg Glu Trp Leu Tyr His Leu Gly Val Pro Val Glu Glu
        435                 440                 445

Ile Asp Glu Leu Ala Ala Thr Gly Ala Lys Thr Val Pro Val Met Met
450                 455                 460

Pro Tyr Ile Thr Ala Phe Phe Met Pro Arg Gln Ala Gly Asp Arg Pro
465                 470                 475                 480

Asp Val Val Pro Asp Gly Ala Val Asn Phe Ala Phe Ile Gly Gln Phe
                485                 490                 495

Ala Glu Ser Lys Gln Arg Asp Cys Ile Phe Thr Thr Glu Tyr Ser Val
            500                 505                 510

Arg Thr Pro Met Glu Ala Val Tyr Thr Leu Leu Asp Ile Glu Arg Gly
        515                 520                 525

Val Pro Glu Val Phe Asn Ser Thr Tyr Asp Val Arg Ser Leu Leu Ala
530                 535                 540

Ala Thr Gly Arg Leu Arg Asp Gly Lys Glu Leu Gly Ile Pro Gly Pro
545                 550                 555                 560

Val Phe Leu Arg Asn Leu Leu Met Asn Lys Leu Asp Lys Thr Gln Ile
                565                 570                 575

Gly Gly Leu Leu Arg Glu Phe Lys Leu Val Gln Glu Asp
            580                 585
```

<210> SEQ ID NO 3
<211> LENGTH: 646
<212> TYPE: PRT
<213> ORGANISM: Elizabethkingia meningoseptica
<220> FEATURE:
<221> NAME/KEY: MISC_FEATURE
<222> LOCATION: (1)..(646)
<223> OTHER INFORMATION: Abbreviated in Fig. 1 as ohyA

<400> SEQUENCE: 3

```
Met Asn Pro Ile Thr Ser Lys Phe Asp Lys Val Leu Asn Ala Ser Ser
1               5                   10                  15

Glu Tyr Gly His Val Asn His Glu Pro Asp Ser Ser Lys Glu Gln Gln
            20                  25                  30

Arg Asn Thr Pro Gln Lys Ser Met Pro Phe Ser Asp Gln Ile Gly Asn
        35                  40                  45

Tyr Gln Arg Asn Lys Gly Ile Pro Val Gln Ser Tyr Asp Asn Ser Lys
    50                  55                  60

Ile Tyr Ile Ile Gly Ser Gly Ile Ala Gly Met Ser Ala Ala Tyr Tyr
65                  70                  75                  80

Phe Ile Arg Asp Gly His Val Pro Ala Lys Asn Ile Thr Phe Leu Glu
                85                  90                  95

Gln Leu His Ile Asp Gly Gly Ser Leu Asp Gly Ala Gly Asn Pro Thr
            100                 105                 110

Asp Gly Tyr Ile Ile Arg Gly Gly Arg Glu Met Asp Met Thr Tyr Glu
        115                 120                 125
```

-continued

Asn Leu Trp Asp Met Phe Gln Asp Ile Pro Ala Leu Glu Met Pro Ala
130                 135                 140

Pro Tyr Ser Val Leu Asp Glu Tyr Arg Leu Ile Asn Asp Asn Asp Ser
145                 150                 155                 160

Asn Tyr Ser Lys Ala Arg Leu Ile Asn Asn Lys Gly Glu Ile Lys Asp
            165                 170                 175

Phe Ser Lys Phe Gly Leu Asn Lys Met Asp Gln Leu Ala Ile Ile Arg
            180                 185                 190

Leu Leu Leu Lys Asn Lys Glu Glu Leu Asp Asp Leu Thr Ile Glu Asp
        195                 200                 205

Tyr Phe Ser Glu Ser Phe Leu Lys Ser Asn Phe Trp Thr Phe Trp Arg
210                 215                 220

Thr Met Phe Ala Phe Glu Asn Trp His Ser Leu Leu Glu Leu Lys Leu
225                 230                 235                 240

Tyr Met His Arg Phe Leu His Ala Ile Asp Gly Leu Asn Asp Leu Ser
                245                 250                 255

Ser Leu Val Phe Pro Lys Tyr Asn Gln Tyr Asp Thr Phe Val Thr Pro
            260                 265                 270

Leu Arg Lys Phe Leu Gln Glu Lys Gly Val Asn Ile His Leu Asn Thr
        275                 280                 285

Leu Val Lys Asp Leu Asp Ile His Ile Asn Thr Glu Gly Lys Val Val
        290                 295                 300

Glu Gly Ile Ile Thr Glu Gln Asp Gly Lys Glu Val Lys Ile Pro Val
305                 310                 315                 320

Gly Lys Asn Asp Tyr Val Ile Val Thr Thr Gly Ser Met Thr Glu Asp
                325                 330                 335

Thr Phe Tyr Gly Asn Asn Lys Thr Ala Pro Ile Ile Gly Ile Asp Asn
                340                 345                 350

Ser Thr Ser Gly Gln Ser Ala Gly Trp Lys Leu Trp Lys Asn Leu Ala
        355                 360                 365

Ala Lys Ser Glu Ile Phe Gly Lys Pro Glu Lys Phe Cys Ser Asn Ile
        370                 375                 380

Glu Lys Ser Ala Trp Glu Ser Ala Thr Leu Thr Cys Lys Pro Ser Ala
385                 390                 395                 400

Leu Ile Asp Lys Leu Lys Glu Tyr Ser Val Asn Asp Pro Tyr Ser Gly
            405                 410                 415

Lys Thr Val Thr Gly Gly Ile Ile Thr Ile Thr Asp Ser Asn Trp Leu
            420                 425                 430

Met Ser Phe Thr Cys Asn Arg Gln Pro His Phe Pro Glu Gln Pro Asp
        435                 440                 445

Asp Val Leu Val Leu Trp Val Tyr Ala Leu Phe Met Asp Lys Glu Gly
450                 455                 460

Asn Tyr Ile Lys Lys Thr Met Leu Glu Cys Thr Gly Asp Glu Ile Leu
465                 470                 475                 480

Ala Glu Leu Cys Tyr His Leu Gly Ile Glu Asp Gln Leu Glu Asn Val
                485                 490                 495

Gln Lys Asn Thr Ile Val Arg Thr Ala Phe Met Pro Tyr Ile Thr Ser
            500                 505                 510

Met Phe Met Pro Arg Ala Lys Gly Asp Arg Pro Arg Val Val Pro Glu
        515                 520                 525

Gly Cys Lys Asn Leu Gly Leu Val Gly Gln Phe Val Glu Thr Asn Asn
        530                 535                 540

Asp Val Val Phe Thr Met Glu Ser Ser Val Arg Thr Ala Arg Ile Ala

```
                545                 550                 555                 560
Val Tyr Lys Leu Leu Asn Leu Asn Lys Gln Val Pro Asp Ile Asn Pro
                    565                 570                 575

Leu Gln Tyr Asp Ile Arg His Leu Leu Lys Ala Ala Lys Thr Leu Asn
                580                 585                 590

Asp Asp Lys Pro Phe Val Gly Glu Gly Leu Leu Arg Lys Val Leu Lys
            595                 600                 605

Gly Thr Tyr Phe Glu His Val Leu Pro Ala Gly Ala Ala Glu Glu Glu
        610                 615                 620

Glu His Glu Ser Phe Ile Ala Glu His Val Asn Lys Phe Arg Glu Trp
625                 630                 635                 640

Val Lys Gly Ile Arg Gly
                    645

<210> SEQ ID NO 4
<211> LENGTH: 589
<212> TYPE: PRT
<213> ORGANISM: Macrococcus caseolyticus
<220> FEATURE:
<221> NAME/KEY: MISC_FEATURE
<222> LOCATION: (1)..(589)
<223> OTHER INFORMATION: Abbreviated in Fig. 1 as Mca

<400> SEQUENCE: 4

Met Tyr Tyr Ser Asn Gly Asn Tyr Glu Ala Phe Ala Arg Pro Lys Lys
1               5                   10                  15

Pro Glu Gly Val Asp Asn Lys Ser Ala Tyr Leu Val Gly Ser Gly Leu
            20                  25                  30

Ala Ser Leu Ala Ala Ala Ser Phe Leu Ile Arg Asp Gly Gln Met Lys
        35                  40                  45

Gly Glu Asn Ile His Ile Leu Glu Glu Leu Asp Leu Pro Gly Gly Ser
    50                  55                  60

Leu Asp Gly Ile Leu Asn Pro Glu Arg Gly Tyr Ile Met Arg Gly Gly
65                  70                  75                  80

Arg Glu Met Glu Asn His Phe Glu Cys Leu Trp Asp Leu Phe Arg Ser
                85                  90                  95

Val Pro Ser Leu Glu Val Glu Asp Ala Ser Val Leu Asp Glu Phe Tyr
            100                 105                 110

Trp Leu Asn Lys Glu Asp Pro Asn Tyr Ser Lys Cys Arg Val Ile Glu
        115                 120                 125

Asn Arg Gly Gln Arg Leu Glu Ser Asp Gly Lys Met Thr Leu Thr Lys
    130                 135                 140

Lys Ala Asn Lys Glu Ile Ile Gln Leu Cys Leu Met Lys Glu Glu Gln
145                 150                 155                 160

Leu Asn Asp Val Lys Ile Ser Asp Val Phe Ser Lys Asp Phe Leu Asp
                165                 170                 175

Ser Asn Phe Trp Ile Tyr Trp Lys Thr Met Phe Ala Phe Glu Pro Trp
            180                 185                 190

His Ser Ala Met Glu Met Arg Arg Tyr Leu Met Arg Phe Ile His His
        195                 200                 205

Ile Gly Gly Leu Ala Asp Phe Ser Ala Leu Lys Phe Thr Lys Phe Asn
    210                 215                 220

Gln Phe Glu Ser Leu Val Met Pro Leu Ile Glu His Leu Lys Ala Lys
225                 230                 235                 240

Asn Val Thr Phe Glu Tyr Gly Val Thr Val Lys Asn Ile Gln Val Glu
                245                 250                 255
```

Cys Ser Lys Glu Ser Lys Val Ala Lys Ala Ile Asp Ile Val Arg Arg
                260                 265                 270

Gly Asn Glu Glu Ser Ile Pro Leu Thr Glu Asn Asp Leu Val Phe Val
            275                 280                 285

Thr Asn Gly Ser Ile Thr Glu Ser Thr Thr Tyr Gly Asp Asn Asp Thr
        290                 295                 300

Pro Ala Pro Pro Thr Ser Lys Pro Gly Gly Ala Trp Gln Leu Trp Glu
305                 310                 315                 320

Asn Leu Ser Thr Gln Cys Glu Phe Gly Asn Pro Ala Lys Phe Tyr
                325                 330                 335

Lys Asp Leu Pro Glu Lys Ser Trp Phe Val Ser Ala Thr Ala Thr Thr
                340                 345                 350

Asn Asn Lys Glu Val Ile Asp Tyr Ile Gln Lys Ile Cys Lys Arg Asp
            355                 360                 365

Pro Leu Ser Gly Arg Thr Val Thr Gly Gly Ile Val Thr Val Asp Asp
        370                 375                 380

Ser Asn Trp Gln Leu Ser Phe Thr Leu Asn Arg Gln Gln Gln Phe Lys
385                 390                 395                 400

Asn Gln Pro Asp Asp Gln Val Ser Val Trp Ile Tyr Ala Leu Tyr Ser
                405                 410                 415

Asp Glu Arg Gly Glu Arg Thr Asn Lys Thr Ile Val Glu Cys Ser Gly
                420                 425                 430

Lys Glu Ile Cys Glu Glu Trp Leu Tyr His Met Gly Val Pro Glu Glu
                435                 440                 445

Lys Ile Ser Ala Leu Ala Ala Glu Cys Asn Thr Ile Pro Ser Tyr Met
    450                 455                 460

Pro Tyr Ile Thr Ala Tyr Phe Met Pro Arg Lys Glu Gly Asp Arg Pro
465                 470                 475                 480

Leu Val Val Pro His Gly Ser Lys Asn Ile Ala Phe Ile Gly Asn Phe
                485                 490                 495

Ala Glu Thr Glu Arg Asp Thr Val Phe Thr Thr Glu Tyr Ser Val Arg
                500                 505                 510

Thr Ala Met Glu Ala Val Tyr Lys Leu Leu Glu Val Asp Arg Gly Val
            515                 520                 525

Pro Glu Val Phe Ala Ser Val Tyr Asp Val Arg Ile Leu Leu His Ala
        530                 535                 540

Leu Ser Val Leu Asn Asp Gly Lys Lys Leu Asp Glu Ile Asp Met Pro
545                 550                 555                 560

Phe Tyr Glu Arg Leu Val Glu Lys Arg Leu Leu Lys Lys Ala Ser Gly
                565                 570                 575

Thr Phe Ile Glu Glu Leu Leu Glu Glu Ala Asn Leu Ile
            580                 585

<210> SEQ ID NO 5
<211> LENGTH: 625
<212> TYPE: PRT
<213> ORGANISM: Bifidobacterium breve
<220> FEATURE:
<221> NAME/KEY: MISC_FEATURE
<222> LOCATION: (1)..(625)
<223> OTHER INFORMATION: Abbreviated in Fig. 1 as Bbr

<400> SEQUENCE: 5

Met Tyr Tyr Ser Ser Gly Asn Tyr Glu Ala Phe Ala Arg Pro Lys Lys
1               5                   10                  15

-continued

Pro Ala Gly Val Asp Ser Lys His Ala Tyr Ile Ile Gly Thr Gly Leu
            20                  25                  30

Ala Ala Leu Ser Ser Ala Cys Tyr Leu Val Arg Asp Gly Gln Met Pro
        35                  40                  45

Gly Asp His Ile His Ile Leu Glu Lys Asp Pro Val Pro Gly Gly Ala
    50                  55                  60

Cys Asp Gly Leu Asp Ile Pro Gly Leu Gly Tyr Val Met Arg Gly Gly
65                  70                  75                  80

Arg Glu Met Asp Asn His Phe Glu Val Met Trp Asp Leu Phe Arg Ser
                85                  90                  95

Ile Pro Ser Ile Glu Thr Glu Gly Val Ser Val Leu Asp Glu Tyr Tyr
            100                 105                 110

Trp Leu Asn Lys Glu Asp Pro Asn Tyr Ser Leu Cys Arg Ala Thr Lys
        115                 120                 125

Asp Leu Gly Lys Asp Ala Gly Leu Lys Gly Lys Phe Gly Leu Ser Asp
    130                 135                 140

Lys Ala Ser Met Glu Ile Met Lys Leu Phe Phe Thr Pro Asp Glu Asp
145                 150                 155                 160

Leu Tyr Asp Lys Pro Ile Thr Asp Phe Phe Asp Asp Glu Val Leu Asn
                165                 170                 175

Ser Asn Phe Trp Leu Tyr Trp Arg Thr Met Phe Ala Phe Glu Asn Trp
            180                 185                 190

His Ser Ala Leu Glu Met Lys Leu Tyr Ile Lys Arg Tyr Ile His His
        195                 200                 205

Ile Gly Gly Leu Pro Asp Phe Ser Ala Leu Arg Phe Thr Arg Tyr Asn
    210                 215                 220

Gln Tyr Glu Ser Met Ile Leu Pro Met Val Lys Tyr Leu Glu Ser His
225                 230                 235                 240

Gly Val Glu Phe Arg Tyr Asn Thr Lys Val Glu Asn Val Glu Phe Ala
                245                 250                 255

Ile Gly Gly Gly Asp Gly Pro Lys Arg Glu His Thr Gly Val Gly Gln
            260                 265                 270

Asp Thr Ile Gln Lys Ile Gln Ala Thr Ser Gly Phe Phe Lys Arg Asn
        275                 280                 285

Pro Ala Ser Thr Pro Thr Lys Lys Leu Ala Val Arg Ile Asp Val Ser
    290                 295                 300

Gln Glu Gly Glu Lys Ser Ser Ile Asp Leu Thr Glu Asn Asp Leu Val
305                 310                 315                 320

Phe Ile Thr Asn Gly Gly Cys Val Glu Asn Ser Thr Met Gly Ser Gln
                325                 330                 335

Asn Ser Pro Ala Ala Trp Asn Pro Asp Leu Lys Pro Gly Gly Gly Trp
            340                 345                 350

Asp Met Trp Arg Arg Ile Ala Glu Gln Asp Pro Ser Phe Gly His Pro
        355                 360                 365

Glu Lys Phe Cys Ser Asp Pro Asn Ala Thr Lys Trp Met Ser Ala Thr
    370                 375                 380

Val Thr Thr Leu Asp Asp Glu Ile Pro Pro Tyr Ile Gln Lys Ile Cys
385                 390                 395                 400

Lys Arg Asp Pro Phe Ser Gly Lys Val Val Thr Gly Gly Ile Val Thr
                405                 410                 415

Val Gln Asp Ser Asn Trp Leu Met Ser Trp Thr Leu Asn Arg Gln Gln
            420                 425                 430

Gln Phe Arg Asp Gln Pro Lys Asp Gln Leu Cys Val Trp Val Tyr Gly

-continued

```
        435                 440                 445

Leu Phe Pro Asp Lys Pro Gly Asn Tyr Val Lys Lys Pro Met Thr Glu
    450                 455                 460

Cys Thr Gly Glu Glu Ile Cys Glu Glu Trp Leu Tyr His Met Gly Val
465                 470                 475                 480

Pro Thr Asp Lys Ile Glu Ser Leu Ala Lys His His Ala Asn Thr Val
                485                 490                 495

Pro Val Met Met Pro Tyr Ile Thr Ala Phe Phe Met Pro Arg Ala Ala
            500                 505                 510

Gly Asp Arg Pro Asp Val Val Pro Asp Gly Ala Val Asn Phe Ala Phe
        515                 520                 525

Leu Gly Gln Phe Ala Glu Thr Pro Arg Asp Thr Ile Phe Thr Thr Glu
    530                 535                 540

Tyr Ser Met Arg Thr Gly Met Glu Ala Val Tyr Thr Leu Leu Gly Val
545                 550                 555                 560

Asp Arg Gly Val Pro Glu Val Trp Gly Ser Val Tyr Asp Val Arg Asn
                565                 570                 575

Leu Leu Asn Ala Thr Val Lys Leu Arg Asp Gly Ala Pro Val Thr Asp
            580                 585                 590

Met Lys Leu Asn Phe Ile Glu Lys Ala Val Val Lys Lys Val Leu Lys
        595                 600                 605

Lys Leu Asp Gly Thr Asp Ile Ala Thr Leu Leu Arg Glu Tyr His Val
    610                 615                 620

Ile
625

<210> SEQ ID NO 6
<211> LENGTH: 591
<212> TYPE: PRT
<213> ORGANISM: Corynebacterium kroppenstedtii
<220> FEATURE:
<221> NAME/KEY: MISC_FEATURE
<222> LOCATION: (1)..(591)
<223> OTHER INFORMATION: Abbreviated in Fig. 1 as Ckr

<400> SEQUENCE: 6

Met Ser Ile Tyr Gln Ser Thr Tyr Pro Thr Asp Gln Phe Gly Asn Arg
1               5                   10                  15

Phe Val Gln Asn Asp Met Gly Lys Tyr Ile Glu Thr Arg Pro Glu Val
            20                  25                  30

Ser Ser Asp Ile Lys Asp Arg Lys Ala Tyr Phe Val Gly Ser Gly Ile
        35                  40                  45

Gly Asn Leu Ile Ala Ala Gly Tyr Leu Leu Arg Asp Gly Gln Met Pro
    50                  55                  60

Gly Glu Asn Ile Thr Phe Leu Glu Gln Leu Asp Val Ala Gly Gly Ser
65                  70                  75                  80

Phe Asp Gly Ala Gly Asn Asn Gln Glu Gly Phe Ile Ala Arg Gly Gly
                85                  90                  95

Arg Glu Met Gly Gln His Phe Glu Cys Phe Trp Asp Ile Met Lys Asp
            100                 105                 110

Val Pro Ala Ile Glu Met Pro Ala Pro His Thr Val Leu Asp Glu Phe
        115                 120                 125

Asn Lys Val Asn Glu Glu Asp Pro Asn Ile Ser Asn Cys Arg Ile Ile
    130                 135                 140

Ser Asn Gln Ala Gln Thr Arg Leu Lys Asn Pro Lys Leu Glu Leu Ser
145                 150                 155                 160
```

```
Lys Lys Ala Gln Leu Gln Ile Val Lys Leu Leu Ala Lys Glu Glu
            165                 170                 175

Asp Thr Tyr Tyr Lys Thr Ile Glu Asp Trp Phe Gly Lys Asp Phe Leu
        180                 185                 190

Glu Ser Asn Phe Tyr Thr Leu Trp Arg Ser Met Phe Ala Phe Gln Asp
            195                 200                 205

Tyr Gln Ser Leu Thr Glu Met Lys Arg Tyr Phe His Arg Phe Leu Gln
        210                 215                 220

Tyr Leu Pro Gly Phe Ser Asp Phe Ser Cys Leu Arg Phe Ser Lys Tyr
225                 230                 235                 240

Asn Gln Phe Thr Ser Phe Ile Glu Pro Leu Arg Asn Phe Leu Lys Glu
            245                 250                 255

Lys Gly Val Lys Phe Gln Tyr Gly Thr Cys Val Lys Asp Leu Asp Ile
        260                 265                 270

Asp Val Lys Gly Ser Ser Phe Thr Val Thr Gly Ile Val Thr Asn Lys
    275                 280                 285

Glu Thr Ile Pro Thr Arg Ser Gln Asp Ile Val Ile Val Thr Asn Gly
        290                 295                 300

Ser Leu Thr Glu Ser Thr Gly Tyr Gly Asp Met Asn Thr Val Pro Glu
305                 310                 315                 320

Phe Lys Lys Thr Pro Gly Pro Ala Trp Ser Leu Trp Lys Asn Ile Ala
            325                 330                 335

Glu Lys Ala Pro Asn Cys Gly Arg Pro Glu Arg Phe Cys Ser Asp Pro
        340                 345                 350

Glu Ser Thr Val Trp Glu Ser Ile Ser Phe Asn Phe Tyr Asp Gly Tyr
    355                 360                 365

Asp Asn Pro Phe Thr Gln Lys Leu Lys Glu Leu Thr His Arg Asp Val
    370                 375                 380

Phe Asn Gly Arg Ala Val Thr Ala Gly Ile Ile Thr Ala Gln Asp Ser
385                 390                 395                 400

Pro Trp Leu Cys Ser Leu Thr Val His Arg Gln Pro Gln Phe Pro Gly
            405                 410                 415

Gln Gln Asp Gly Leu Cys Val Ala Trp Ala Tyr Gly Leu His Trp Trp
        420                 425                 430

Lys Lys Gly Thr Val Thr Gly Lys Pro Met Leu Glu Cys Thr Gly Glu
    435                 440                 445

Glu Ile Leu Arg Glu Phe Cys Tyr His Phe Gly Val Val Asp Val Glu
        450                 455                 460

Lys Thr Ile Lys His Thr Lys Val Arg Leu Ala Val Met Pro Tyr Ile
465                 470                 475                 480

Thr Ser Glu Phe Val Pro Arg Gly Ala Gly Asp Arg Pro Asp Pro Val
            485                 490                 495

Pro Ala Gly Ser Thr Asn Leu Gly Phe Thr Gly Gln Phe Val Glu Thr
        500                 505                 510

Pro Asp Asp Cys Val Phe Thr Thr Glu Gly Ser Ala Arg Thr Gly Gln
    515                 520                 525

Met Ala Val Tyr Gly Leu Leu Asn Leu Lys Arg Asp Ile Pro Pro Ile
530                 535                 540

Tyr Pro Val Gln Tyr Asp Ile Arg Ala Leu Leu His Ser Ala Ser Ala
545                 550                 555                 560

Met Asn Asp Gly Lys Leu Pro Gly Glu Lys Leu Leu Arg Lys Phe Leu
            565                 570                 575
```

-continued

```
Lys Asn Thr Tyr Tyr Glu Asn Ile Ile Pro Lys Gly Ser Ser His
            580                 585                 590
```

<210> SEQ ID NO 7
<211> LENGTH: 591
<212> TYPE: PRT
<213> ORGANISM: Ochrobactrum anthropi
<220> FEATURE:
<221> NAME/KEY: MISC_FEATURE
<222> LOCATION: (1)..(591)
<223> OTHER INFORMATION: Abbreviated in Fig. 1 as Oan

<400> SEQUENCE: 7

```
Met Tyr Arg Ser Asn Gly Asn Phe Glu Ala Tyr Ala Arg Pro Pro Lys
1               5                   10                  15

Pro Glu Gly Val Asp Gly Lys Thr Ala Tyr Phe Val Gly Ala Gly Leu
            20                  25                  30

Ala Ser Leu Ala Gly Ala Ala Phe Leu Ile Arg Asp Ala Gln Leu Ser
        35                  40                  45

Gly Glu Asn Ile Ile Ile Phe Glu Glu Leu Ala Leu Pro Gly Gly Ser
    50                  55                  60

Met Asp Gly Ile Leu Asp Glu His Lys Gly Phe Ile Val Arg Gly Gly
65                  70                  75                  80

Arg Glu Met Glu Ala His Phe Glu Thr Leu Trp Asp Leu Phe Arg Ser
                85                  90                  95

Ile Pro Ser Leu Asp Thr Pro Asp Ala Ser Val Leu Asp Glu Met Tyr
            100                 105                 110

Trp Leu His Lys Lys Asp Pro Ser Arg Asn Pro Cys Arg Ala Thr Glu
        115                 120                 125

Gly Arg Gly Asp Pro Ile Pro His Met Ala Asp Leu Thr Leu Thr Pro
    130                 135                 140

Lys Ala Val Glu Glu Met Leu Lys Leu Ala Leu Thr Pro Glu Ser Ala
145                 150                 155                 160

Leu Asp Asp Lys Arg Ile Asp Glu Cys Phe Gly Glu Glu Phe Phe Ala
                165                 170                 175

Ser Asn Phe Trp Leu Tyr Trp Ala Thr Met Phe Ala Phe Glu Pro Trp
            180                 185                 190

Ala Ser Ala Met Glu Met Arg Arg Tyr Ile Leu Arg Phe Val His His
        195                 200                 205

Ile Ala Thr Leu Ala Asp Leu Ser Ser Leu Arg Phe Thr Arg Tyr Asn
    210                 215                 220

Gln Tyr Glu Ser Leu Ile Met Pro Leu Val Ala Trp Leu Glu Gly Lys
225                 230                 235                 240

Gly Val Arg Phe Gln Tyr Asp Thr Gln Val Glu Asn Ile Glu Val Glu
                245                 250                 255

Thr Ala Gly Gly Asn Lys Leu Ala Arg Arg Leu Val Met Thr Val Gly
            260                 265                 270

Gly Glu Pro Lys Thr Ile Glu Leu Thr Glu Asn Asp Val Val Phe Val
        275                 280                 285

Thr Asn Gly Ser Ile Thr Glu Ser Ser Thr Phe Gly Asp Asn Asp His
    290                 295                 300

Pro Ala Pro Ile Glu Thr Gly His Gly Gly Ala Trp Thr Leu Trp Lys
305                 310                 315                 320

Asn Leu Ala Ala Gln His Pro Ala Phe Gly Arg Pro Glu Lys Phe Cys
                325                 330                 335

Glu Asp Ile Pro Asp Ala Asn Trp Thr Ile Ser Ala Thr Val Thr Leu
```

```
            340                 345                 350
Leu Asp Asp Lys Ile Val Pro Trp Ile Glu Lys Met Thr Gly Arg Asp
            355                 360                 365

Pro Arg Asp Gly Arg Ile Val Thr Gly Pro Cys Asn Phe Lys Asp
        370                 375                 380

Ser Asn Trp Leu Tyr Gly Tyr Thr Met Ser Arg Gln Pro His Phe Lys
385                 390                 395                 400

Ala Gln Asp Glu Ser Gln Lys Leu Val Val Trp Leu Tyr Gly Leu Phe
                405                 410                 415

Ser Asp Lys Pro Gly Asn Tyr Val Lys Lys Ile Arg Glu Cys Ala
            420                 425                 430

Gly Ala Glu Leu Cys Glu Glu Trp Leu Phe His Met Gly Val Pro Val
            435                 440                 445

Glu Asp Ile Pro Ala Leu Ala Arg Arg Ser Ala Ser Thr Val Pro Cys
        450                 455                 460

Asn Met Pro Tyr Ile Thr Ser Tyr Phe Met Pro Arg Ala Met Gly Asp
465                 470                 475                 480

Arg Pro Leu Val Val Pro Asp Gly Ser Lys Asn Leu Ala Phe Ile Gly
                485                 490                 495

Asn Phe Ala Glu Thr Glu Lys Asp Thr Val Phe Thr Thr Glu Tyr Ser
            500                 505                 510

Val Arg Thr Ala Met Glu Ala Val Tyr Thr Leu Phe Asn Val Asp Arg
            515                 520                 525

Gly Val Pro Glu Val Phe Ala Ser Ser Phe Asp Val Arg Val Leu Met
        530                 535                 540

Ser Ala Leu Tyr Tyr Leu Asn Asp Arg Lys Lys Leu Asp Glu Ile Gln
545                 550                 555                 560

Leu Pro Phe Val Ala Arg Leu Leu Gly Lys Val Ala Met Lys Lys Ile
                565                 570                 575

Glu Gly Thr Tyr Leu Glu Glu Leu Leu Lys Asp Ala Lys Leu Val
            580                 585                 590

<210> SEQ ID NO 8
<211> LENGTH: 646
<212> TYPE: PRT
<213> ORGANISM: Myroides odoratus
<220> FEATURE:
<221> NAME/KEY: MISC_FEATURE
<222> LOCATION: (1)..(646)
<223> OTHER INFORMATION: Abbreviated in Fig. 1 as Mod

<400> SEQUENCE: 8

Met Lys Val Asp Thr Gln Lys Phe Asp Lys Ile Leu Glu Thr Ser Ser
1               5                   10                  15

Lys Tyr Gly His Val Asn Gln Ala Pro Asn Gly Asn Thr Glu Pro Pro
                20                  25                  30

Ile Asn Thr Ala Gln Arg Ser Met Pro Phe Ala Asp Glu Pro Gly Asn
            35                  40                  45

Tyr Gln Arg Asn Lys Gly Ile Pro Ser Lys Asp Phe Ser Gln Ser Lys
        50                  55                  60

Val Tyr Ile Ile Gly Ser Gly Ile Ala Gly Met Ala Ala Ala Tyr Tyr
65                  70                  75                  80

Phe Ile Arg Asp Gly Arg Ile Pro Ala Ala Asn Ile Thr Phe Leu Glu
                85                  90                  95

Gln Leu Ser Ile Asp Gly Gly Ser Leu Asp Gly Ala Gly Asn Ala Gln
            100                 105                 110
```

```
Glu Gly Tyr Ile Val Arg Gly Gly Arg Glu Met Asp Met Thr Tyr Glu
            115                 120                 125

Asn Leu Trp Asp Ile Phe Gln Asp Ile Pro Ala Leu Glu Leu Pro Lys
            130                 135                 140

Pro Tyr Ser Val Leu Asp Glu Tyr Arg Leu Ile Asn Asp Asn Asp Pro
145                 150                 155                 160

Asn Tyr Ser Lys Ser Arg Phe Ile His Gln Leu Gly Glu Ile Lys Asp
            165                 170                 175

Phe Ser Gln Phe Gly Leu Ser Lys Lys Asp Gln Met Ala Leu Ile Lys
            180                 185                 190

Leu Leu Leu Lys Arg Lys Glu Glu Leu Asp Asp Ile Thr Ile Glu Gln
            195                 200                 205

Tyr Phe His Ser Ser Phe Leu Glu Ser Asn Phe Trp Thr Phe Trp Arg
            210                 215                 220

Thr Met Phe Ala Phe Glu Asn Trp His Ser Leu Leu Glu Phe Lys Leu
225                 230                 235                 240

Tyr Met His Arg Phe Leu His Asp Ile Asp Gly Leu Lys Asp Leu Ser
            245                 250                 255

Ala Leu Val Phe Pro Arg Tyr Asn Gln Tyr Asp Thr Phe Val Ala Pro
            260                 265                 270

Leu Arg Asn His Leu Thr Glu Leu Gly Val Gln Ile Arg Leu Asp Thr
            275                 280                 285

Leu Val His Asp Val Asp Leu His Ser Thr Thr Ala Gly Lys Leu Val
            290                 295                 300

Lys Gly Leu Leu Val Asn Gln Gly Gln Thr Arg Ile Glu Met
305                 310                 315                 320

Asn Glu Gln Asp Phe Val Val Ile Thr Thr Gly Ser Met Thr Glu Asp
            325                 330                 335

Thr Ser Tyr Gly Thr Asn Thr Thr Val Pro Ile Pro Lys Val Asp Asn
            340                 345                 350

Thr Thr Ser Gly Lys Ser Pro Gly Trp Ser Leu Trp Lys Asn Leu Ala
            355                 360                 365

Ala Lys Ser Pro Val Phe Gly Arg Pro Glu Lys Phe Cys Ser Asn Ile
            370                 375                 380

Glu Lys Ser Ser Trp Glu Ser Ala Thr Leu Thr Cys Lys Pro Ser Pro
385                 390                 395                 400

Leu Ile Asp Lys Leu Lys Glu Tyr Ala Val Asn Asp Pro Tyr Ser Gly
            405                 410                 415

Lys Thr Val Thr Gly Gly Ile Ile Thr Ile Thr Asp Ser Asn Trp Leu
            420                 425                 430

Met Ser Phe Thr Cys Asn Arg Gln Pro His Phe Pro Thr Gln Pro Asp
            435                 440                 445

Asp Ile Leu Val Leu Trp Val Tyr Ala Leu Phe Met Asp Lys Asp Gly
450                 455                 460

Asn Tyr Val Lys Lys Thr Met Pro Ala Cys Thr Gly Asn Glu Ile Leu
465                 470                 475                 480

Ala Glu Leu Cys Tyr His Leu Gly Ile Ile Asp Ser Leu Asn Gln Val
            485                 490                 495

Val Glu Asn Thr Ile Val Arg Thr Ala Tyr Met Pro Tyr Ile Thr Ser
            500                 505                 510

Met Phe Met Pro Arg Ala Gln Gly Asp Arg Pro Gln Val Val Pro Glu
            515                 520                 525
```

```
Gly Cys Leu Asn Leu Gly Leu Ile Gly Gln Phe Val Glu Thr His Asn
            530                 535                 540

Asp Val Val Phe Thr Met Glu Ser Ser Val Arg Thr Gly Arg Gln Ala
545                 550                 555                 560

Val Tyr Gln Leu Leu Asn Leu Asn Lys Gln Val Pro Asp Ile Phe Pro
                565                 570                 575

Leu Gln Tyr Asp Ile Arg His Leu Leu Lys Ala Ala His Ala Leu Asn
            580                 585                 590

Asp Asp Gln Pro Ile Val Gly Glu Ala Leu Leu Arg Lys Phe Leu Gln
            595                 600                 605

Gly Thr Tyr Tyr Glu His Ile Leu Pro Thr Val Glu Lys Arg Lys Asp
610                 615                 620

Asp Gln Glu Ser Phe Phe Val Glu Gln Tyr Glu Lys Ala Lys Asp Trp
625                 630                 635                 640

Phe Lys Lys Leu Ile Gly
                645

<210> SEQ ID NO 9
<211> LENGTH: 591
<212> TYPE: PRT
<213> ORGANISM: Staphylococcus aureus
<220> FEATURE:
<221> NAME/KEY: MISC_FEATURE
<222> LOCATION: (1)..(591)
<223> OTHER INFORMATION: Abbreviated in Fig. 1 as Sau

<400> SEQUENCE: 9

Met Tyr Tyr Ser Tyr Glu Asn Tyr Glu Ala Phe Ala Arg Pro Lys Lys
1               5                   10                  15

Pro Glu Asn Val Glu Asn Lys Ser Ala Tyr Leu Ile Gly Ser Gly Leu
                20                  25                  30

Ala Ser Leu Ala Ala Ala Cys Phe Leu Ile Arg Asp Gly Gln Met Glu
            35                  40                  45

Gly Ser Lys Ile His Ile Leu Glu Glu Leu Pro Lys Ala Gly Gly Ser
        50                  55                  60

Leu Asp Gly Glu Asn Met Pro Leu Lys Gly Tyr Val Val Arg Gly Gly
65                  70                  75                  80

Arg Glu Met Glu Asn His Phe Glu Cys Leu Trp Asp Leu Phe Arg Ser
                85                  90                  95

Ile Pro Ser Leu Glu Ile Asp His Ala Ser Val Leu Asp Glu Phe Tyr
                100                 105                 110

Trp Leu Asn Lys Glu Asp Pro Asn Tyr Ser Arg Cys Arg Val Ile Glu
            115                 120                 125

Lys Gln Gly Gln Arg Leu Val Thr Asp Gly Asp Phe Thr Leu Thr Lys
130                 135                 140

Thr Ala Ile Lys Glu Ile Leu Asp Leu Cys Leu Thr Asn Glu Glu Asp
145                 150                 155                 160

Leu Asp Asp Val Lys Ile Thr Asp Val Phe Ser Asp Phe Asn
                165                 170                 175

Ser Asn Phe Trp Ile Tyr Trp Lys Thr Met Phe Ala Phe Glu Pro Trp
            180                 185                 190

His Ser Ala Met Glu Met Arg Arg Tyr Leu Met Arg Phe Val His His
            195                 200                 205

Ile Gly Gly Leu Ala Asp Phe Ser Ala Leu Lys Phe Thr Lys Tyr Asn
        210                 215                 220

Gln Tyr Glu Ser Leu Val Leu Pro Met Val Glu Tyr Leu Lys Ser His
```

```
            225                 230                 235                 240
    Gly Val Gln Phe Glu Tyr Asp Val Lys Val Glu Asp Ile Lys Val Asp
                    245                 250                 255

Val Thr Thr Ser Gln Lys Ile Ala Arg Glu Ile Leu Ile His Arg His
                260                 265                 270

Gly Lys Ala Glu Ser Ile Lys Leu Thr Val Asp Asp Leu Val Phe Val
                275                 280                 285

Thr Asn Gly Ser Ile Thr Glu Ser Ser Thr Tyr Gly Asp Asn Asp Thr
            290                 295                 300

Pro Ala Pro Pro Thr Asp Glu Leu Gly Gly Ser Trp Thr Leu Trp Lys
    305                 310                 315                 320

Asn Leu Ala Arg Gln Ser Pro Glu Phe Gly Asn Pro Asp Lys Phe Cys
                    325                 330                 335

Gln Asn Ile Pro Gln Lys Ser Trp Phe Val Ser Ala Thr Ser Thr Thr
                340                 345                 350

Asn Asn Lys Asp Ile Ile Asp Thr Ile Glu Ser Ile Cys Lys Arg Asp
                355                 360                 365

Pro Leu Ala Gly Lys Thr Val Thr Gly Gly Ile Ile Thr Ile Asn Asp
    370                 375                 380

Ser Ala Trp Gln Ile Ser Phe Thr Ile Asn Arg Gln Gln Gln Phe Lys
    385                 390                 395                 400

Asp Gln Pro Lys Asn Glu Ile Ser Thr Trp Ile Tyr Ala Leu Tyr Ser
                    405                 410                 415

Asp Val Asn Gly Asp Tyr Ile Lys Lys Pro Ile Thr Glu Cys Ser Gly
                420                 425                 430

Asn Glu Ile Cys Gln Glu Trp Leu Tyr His Leu Gly Val Pro Thr Asp
                435                 440                 445

Lys Ile Glu Asp Leu Ala Lys His Ala Ser Asn Thr Ile Pro Val Tyr
            450                 455                 460

Met Pro Tyr Ile Thr Ser Tyr Phe Met Thr Arg Ala Ile Gly Asp Arg
    465                 470                 475                 480

Pro Leu Val Val Pro His Gln Ser Gln Asn Leu Ala Phe Ile Gly Asn
                    485                 490                 495

Phe Ala Glu Thr Glu Arg Asp Thr Val Phe Thr Thr Glu Tyr Ser Val
                500                 505                 510

Arg Thr Ala Met Glu Ala Val Tyr Gln Leu Leu Asn Ile Asp Arg Gly
                515                 520                 525

Ile Pro Glu Val Ile Asn Ser Thr Phe Asp Leu Arg Val Leu Met Asp
    530                 535                 540

Ala Ile Tyr Glu Leu Asn Asp His Gln Asp Leu Arg Glu Ile Thr Lys
    545                 550                 555                 560

Asp Ser Lys Ile Gln Lys Leu Ala Leu Ala Gly Phe Leu Lys Lys Ile
                    565                 570                 575

Lys Gly Thr Tyr Ile Glu Ser Leu Leu Lys Glu His Lys Leu Leu
                580                 585                 590

<210> SEQ ID NO 10
<211> LENGTH: 642
<212> TYPE: PRT
<213> ORGANISM: Chryseobacterium gleum
<220> FEATURE:
<221> NAME/KEY: MISC_FEATURE
<222> LOCATION: (1)..(642)
<223> OTHER INFORMATION: Abbreviated in Fig. 1 as Cgl

<400> SEQUENCE: 10
```

```
Met Ser Thr Ile Asn Ser Lys Phe Asp Lys Val Leu Asn Ala Ser Asp
1               5                   10                  15

Gln Phe Gly Asn Val Asn His Glu Pro Asp Ser Ser Lys Glu Val Gln
            20                  25                  30

Ile Asn Thr Pro Glu Lys Thr Met Pro Phe Ser Asp Gln Ile Gly Asn
            35                  40                  45

Tyr Gln Arg Asn Lys Gly Ile Pro Leu Gln Ser Tyr Glu Asn Ser Lys
50                      55                  60

Ile Tyr Ile Val Gly Ser Gly Ile Ala Gly Met Ser Ala Ala Tyr Tyr
65                  70                  75                  80

Phe Ile Arg Asp Gly Arg Val Pro Gly Lys Asn Ile Ile Phe Leu Asp
                85                  90                  95

Gln Leu Asn Val Glu Gly Gly Ser Leu Asp Gly Ala Gly Asn Ala Lys
                100                 105                 110

Asp Gly Tyr Ile Ile Arg Gly Gly Arg Glu Met Asp Met Thr Tyr Glu
        115                 120                 125

Asn Leu Trp Asp Met Phe Gln Asp Ile Pro Ala Leu Glu Leu Pro Ala
        130                 135                 140

Pro Tyr Ser Val Leu Asp Glu Tyr Arg Leu Val Asn Asp Asn Asp Pro
145                 150                 155                 160

Asn Tyr Ser Lys Ala Arg Leu Ile His Asn Gln Gly Gln Ile Lys Asp
                165                 170                 175

Phe Ser Lys Phe Gly Leu Glu Lys Lys Asp Gln Leu Ala Ile Val Lys
                180                 185                 190

Leu Leu Leu Lys Lys Lys Glu Leu Asp Asp Leu Thr Ile Glu Asp
                195                 200                 205

Tyr Phe Ser Glu Ser Phe Leu Asn Ser Asn Phe Trp Phe Phe Trp Arg
        210                 215                 220

Ser Met Phe Ala Phe Glu Asn Trp His Ser Leu Leu Glu Leu Lys Leu
225                 230                 235                 240

Tyr Met His Arg Phe Leu His Ala Ile Asp Gly Met Lys Asp Phe Ser
                245                 250                 255

Cys Leu Val Phe Pro Lys Tyr Asn Gln Tyr Asp Thr Tyr Val Thr Pro
                260                 265                 270

Leu Lys Asn Phe Leu Val Glu Lys Gly Val Gln Ile Gln Phe Asn Thr
        275                 280                 285

Leu Val Lys Asp Leu Asp Ile His Ile Asn Thr Glu Gly Lys Thr Val
        290                 295                 300

Glu Gly Ile Ile Thr Glu Gln Asn Gly Glu Glu Val Lys Ile Pro Ile
305                 310                 315                 320

Ser Lys Glu Asp Tyr Val Ile Val Thr Thr Gly Ser Met Thr Glu Ser
                325                 330                 335

Thr Phe Tyr Gly Asp Asn Asn Thr Val Pro Glu Val Thr Ile Asp Asn
                340                 345                 350

Ser Ser Ala Gly Gln Ser Ala Gly Trp Lys Leu Trp Lys Asn Leu Ala
                355                 360                 365

Ala Lys Ser Glu Val Phe Gly Lys Pro Glu Lys Phe Cys Ser His Ile
        370                 375                 380

Glu Lys Ser Ser Trp Glu Ser Ala Thr Leu Thr Cys Arg Pro Ser Ala
385                 390                 395                 400

Phe Thr Glu Lys Leu Lys Glu Leu Cys Val Asn Asp Pro Tyr Ser Gly
                405                 410                 415
```

-continued

```
Arg Thr Ala Thr Gly Gly Ile Ile Thr Ile Thr Asp Ser Asn Trp Val
            420                 425                 430

Met Ser Phe Thr Cys Asn Arg Gln Pro His Phe Pro Thr Gln Pro Asp
        435                 440                 445

Asp Ile Leu Val Val Trp Val Tyr Ala Leu Leu Met Asp Lys Glu Gly
    450                 455                 460

Asn Tyr Ile Lys Lys Thr Met Pro Gln Cys Thr Gly Asn Glu Ile Leu
465                 470                 475                 480

Ala Glu Leu Cys Tyr His Leu Gly Ile Thr Asp Gln Leu Asp Asn Val
                485                 490                 495

Thr Glu Asn Thr Ile Val Arg Thr Ala Phe Met Pro Tyr Ile Thr Ser
            500                 505                 510

Met Phe Met Pro Arg Ala Met Gly Asp Arg Pro Arg Val Val Pro Glu
        515                 520                 525

Gly Cys Thr Asn Leu Gly Leu Val Gly Gln Phe Val Glu Thr Asn Asn
    530                 535                 540

Asp Val Val Phe Thr Met Glu Ser Ser Val Arg Thr Ala Arg Ile Ala
545                 550                 555                 560

Val Tyr Asn Leu Leu Asn Leu Asn Lys Gln Val Pro Asp Ile Asn Pro
                565                 570                 575

Leu Gln Tyr Asp Ile Arg His Leu Leu Lys Ala Thr Gln Ala Leu Asn
            580                 585                 590

Asp Tyr Lys Pro Phe Leu Gly Glu Gly Ile Leu Arg Lys Ile Leu Lys
        595                 600                 605

Gly Thr Tyr Phe Glu His Ile Leu Val Asn Arg Pro Glu Glu Lys Glu
    610                 615                 620

Glu His Glu Ser Phe Leu Thr Arg Phe Gln Glu Trp Val Lys Gly Val
625                 630                 635                 640

Lys Asp

<210> SEQ ID NO 11
<211> LENGTH: 646
<212> TYPE: PRT
<213> ORGANISM: Cellulophaga algicola
<220> FEATURE:
<221> NAME/KEY: MISC_FEATURE
<222> LOCATION: (1)..(646)
<223> OTHER INFORMATION: Abbreviated in Fig. 1 as Cal

<400> SEQUENCE: 11

Met Gly Lys Ile Thr Glu Lys Phe Asp Lys Val Leu Asn Ala Ser Pro
1               5                   10                  15

Phe Pro Gly His Ile Asp His Ala Pro Asp Ala Ser Lys Glu Val Val
            20                  25                  30

Arg Asn Ser Lys Asp Gln Pro Met Pro Phe Ala Asp Leu Lys Gly Asn
        35                  40                  45

Tyr Gln Arg Asn Lys Gly Ile Pro Ser Lys Ser Phe Lys Asp Ser Lys
    50                  55                  60

Val Tyr Ile Val Gly Thr Gly Ile Ala Gly Leu Ser Ala Ala Tyr Tyr
65                  70                  75                  80

Phe Ile Arg Asp Gly His Ile Pro Gly Glu Asn Ile Ile Phe Leu Asp
                85                  90                  95

Lys Ile Ala Ile Glu Gly Gly Ser Leu Asp Gly Ser Gly Asn Ala Lys
            100                 105                 110

Asp Gly Tyr Leu Ile Arg Gly Gly Arg Glu Leu Glu Met Asn Tyr Glu
        115                 120                 125
```

```
Asn Leu Trp Asp Ile Phe Gln Asp Ile Pro Ala Leu Glu Met Pro Ala
    130                 135                 140

Pro Tyr Ser Val Leu Asp Glu Phe Arg Leu Leu Asn Asp Asn Asp Pro
145                 150                 155                 160

Asn Tyr Ser Lys Ala Arg Leu Ile His Asn Asn Gly Glu Ile Gln Asp
                165                 170                 175

Phe Ser Lys Phe Gly Leu Asp Lys Leu Asp Gln Leu Ala Ile Val Lys
            180                 185                 190

Leu Leu Leu Lys Lys Lys Glu Glu Leu Asp Asp Val Thr Val Glu Ser
        195                 200                 205

Tyr Phe Ser Asp Ser Phe Phe Lys Ser Asn Phe Trp Thr Leu Phe Arg
    210                 215                 220

Thr Met Phe Ala Phe Glu Asn Trp His Ser Leu Leu Glu Cys Lys Leu
225                 230                 235                 240

Tyr Met His Arg Phe Leu His Arg Ile Asp Gly Phe Asn Asp Leu Ser
                245                 250                 255

Cys Leu Val Phe Pro Lys Tyr Asn Gln His Asp Thr Phe Val Lys Pro
            260                 265                 270

Leu Thr Asp His Leu Lys Ser Lys Gly Val Lys Ile Gln Phe Asn Thr
        275                 280                 285

Phe Val Lys Asp Leu Glu Val Gln Ile Asn Thr Glu Gly Lys Val Val
    290                 295                 300

Lys Gly Ile Ile Thr Gln Gln Glu Asp Lys Glu Val Thr Ile Ala Val
305                 310                 315                 320

Thr Glu Asn Asp Phe Val Ile Val Thr Thr Gly Ser Met Thr Glu Asp
                325                 330                 335

Thr His Tyr Gly Asp Asn Ile Asn Ala Pro Ile Val Ala Ile Asp Asp
            340                 345                 350

Ile Lys Ser Gly Glu Ser Asp Gly Trp Gln Leu Trp Lys Asn Leu Ala
        355                 360                 365

Thr Lys Ser Ile Glu Phe Gly Lys Pro Glu Lys Phe Tyr Ser Ser Val
    370                 375                 380

Lys Lys Ser Ser Trp Glu Ser Ala Thr Leu Thr Cys Arg Pro Ser Ala
385                 390                 395                 400

Phe Thr Glu Lys Ile Lys Glu Tyr Cys Val Asn Asp Pro Tyr Ser Gly
                405                 410                 415

Lys Ser Ala Thr Gly Gly Ile Val Thr Ile Thr Asp Ser Asn Trp Leu
            420                 425                 430

Met Ser Phe Thr Ile Asn Arg Gln Pro His Phe Pro Glu Gln Pro Asp
        435                 440                 445

Asp Ile Leu Val Ile Trp Val Tyr Ala Leu Phe Met Asp Lys Asn Gly
    450                 455                 460

Asn Tyr Ser Lys Lys Thr Met Pro Gln Cys Thr Gly Asn Glu Val Leu
465                 470                 475                 480

Ala Glu Leu Cys Phe His Ile Gly Leu Glu Asp Gln Ile Ala Thr Ile
                485                 490                 495

Ile Lys Asn Thr Ile Val Lys Thr Ser Phe Met Pro Tyr Ile Thr Ser
            500                 505                 510

Met Phe Met Pro Arg Ala Ala Gly Asp Arg Pro Glu Val Val Pro Asn
        515                 520                 525

Gly Ser Lys Asn Leu Gly Leu Val Gly Gln Phe Val Glu Thr His Asn
530                 535                 540
```

```
Asp Val Val Phe Thr Val Asp Ala Ser Ile Arg Thr Ala Arg Ile Ala
545                 550                 555                 560

Val Tyr Lys Leu Leu Asn Leu Asn Lys Gln Val Pro Asp Ile Ala Ala
                565                 570                 575

Gly Gln Tyr Asp Ile Arg Gln Leu Leu Lys Ala Ala Lys Ala Leu Asn
            580                 585                 590

Asp Tyr Lys Pro Phe Pro Gly Glu Ser Val Leu Lys Arg Val Leu Lys
            595                 600                 605

Asn Thr Tyr Phe Glu His Ile Leu Pro Glu Gly Val Glu Asp Glu Glu
            610                 615                 620

Gln His Asp Ser Phe Leu Thr Glu Gln Leu Glu Lys Leu Lys Gly Trp
625                 630                 635                 640

Ala Lys Glu Leu Thr His
                645

<210> SEQ ID NO 12
<211> LENGTH: 591
<212> TYPE: PRT
<213> ORGANISM: Lactobacillus acidophilus
<220> FEATURE:
<221> NAME/KEY: MISC_FEATURE
<222> LOCATION: (1)..(591)
<223> OTHER INFORMATION: Abbreviated in Fig. 1 as Lac

<400> SEQUENCE: 12

Met Tyr Tyr Ser Asn Gly Asn Tyr Glu Ala Phe Ala Asp Pro Lys Lys
1               5                   10                  15

Pro Ala Gly Val Asp Lys Lys Ser Ala Tyr Ile Ile Gly Ser Gly Leu
            20                  25                  30

Ala Gly Leu Ser Thr Ala Val Phe Leu Val Arg Asp Ala Gln Met Lys
        35                  40                  45

Gly Glu Asn Ile His Ile Leu Glu Glu Leu Pro Val Ala Gly Gly Ser
    50                  55                  60

Leu Asp Gly Ala Asp Arg Pro Asn Ala Gly Phe Val Val Arg Gly Gly
65                  70                  75                  80

Arg Glu Met Glu Asn His Phe Glu Cys Leu Trp Asp Met Tyr Arg Ser
                85                  90                  95

Ile Pro Ser Leu Glu Val Pro Gly Ala Ser Tyr Leu Asp Glu Tyr Tyr
            100                 105                 110

Trp Leu Asp Lys Glu Asp Pro Asn Ser Ser Asn Cys Arg Leu Ile Tyr
        115                 120                 125

Asn Arg Gly Asp Arg Leu Pro Ser Asp Gly Gln Tyr Gly Leu Gly Lys
    130                 135                 140

Cys Ala Asn Glu Ile Val Lys Leu Ile Met Thr Pro Glu Lys Glu Ile
145                 150                 155                 160

Glu Gly Gln Thr Ile Glu Glu Phe Phe Ser Asp Glu Phe Phe Lys Thr
                165                 170                 175

Asn Phe Trp Thr Tyr Trp Ser Met Phe Ala Phe Glu Lys Trp His
            180                 185                 190

Ser Leu Ala Glu Met Arg Arg Tyr Ala Met Arg Phe Ile His His Ile
        195                 200                 205

Asp Gly Leu Pro Asp Phe Thr Ala Leu Lys Phe Asn Lys Tyr Asn Gln
    210                 215                 220

Tyr Glu Ser Met Val Lys Pro Leu Leu Ala Tyr Leu Lys Asp His Gly
225                 230                 235                 240

Val Gln Phe Glu Tyr Asp Cys His Val Lys Asn Val Glu Val Asp His
```

```
                        245                 250                 255
Glu Gly Asp Ser Lys Ile Ala Lys Lys Ile Val Met Thr Gln Asn Gly
            260                 265                 270

Lys Asp Lys Glu Ile Asp Leu Thr His Asn Asp Ile Val Phe Val Thr
            275                 280                 285

Asn Gly Ser Ile Thr Glu Ser Ser Thr Tyr Gly Asp Gln Asn Thr Pro
            290                 295                 300

Ala Pro Ile Thr Asn Ala Lys Gly Asp Ser Trp Lys Leu Trp Glu Asn
305                 310                 315                 320

Leu Ala Lys Gln Asp Pro Ala Phe Gly His Pro Asp Val Phe Cys Glu
            325                 330                 335

Asn Leu Pro Glu Arg Ser Trp Phe Val Ser Ala Thr Ala Thr Leu Glu
            340                 345                 350

Asn Lys Lys Leu Ala Pro Tyr Phe Glu Arg Leu Thr Lys Arg Ser Leu
            355                 360                 365

Tyr Asp Gly Lys Val Asn Thr Gly Gly Ile Ile Thr Ile Val Asp Ser
            370                 375                 380

Asn Trp Glu Leu Ser Phe Thr Ile His Arg Gln Pro His Phe Lys Ser
385                 390                 395                 400

Gln Asn Pro Asp Gln Ile Val Val Trp Ile Tyr Ala Leu Tyr Ser Asp
            405                 410                 415

Thr Glu Gly Asn Tyr Ile Lys Lys Arg Ile Val Asp Cys Thr Gly Lys
            420                 425                 430

Glu Ile Ala Glu Glu Leu Leu Tyr His Leu Gly Val Pro Glu Ser Gln
            435                 440                 445

Ile Ser Glu Leu Ala Ser Glu Glu Asn Met Asn Thr Val Pro Val Tyr
450                 455                 460

Met Pro Tyr Ile Thr Ser Tyr Phe Met Pro Arg Arg Asp Gly Asp Arg
465                 470                 475                 480

Pro Asp Val Val Pro Glu Gly Ser Ile Asn Leu Ala Phe Ile Gly Asn
            485                 490                 495

Phe Ala Glu Ser Pro Thr Arg Asp Thr Val Phe Thr Thr Glu Tyr Ser
            500                 505                 510

Val Arg Thr Ala Met Glu Ala Val Tyr Thr Leu Leu Asn Val Asp Arg
            515                 520                 525

Gly Val Pro Glu Val Phe Asp Ser Ile Tyr Asp Ile Arg Gln Leu Leu
            530                 535                 540

Arg Ala Met Tyr Tyr Met Ser Asp Lys Lys Lys Leu Ala Asp Gln Asp
545                 550                 555                 560

Met Pro Leu Pro Glu Lys Leu Ala Val Lys Thr Gly Met Arg Lys Ile
            565                 570                 575

Lys Lys Thr Trp Val Glu Glu Leu Leu Lys Glu Ala Asn Leu Val
            580                 585                 590
```